(12) United States Patent
Park et al.

(10) Patent No.: US 9,833,487 B2
(45) Date of Patent: Dec. 5, 2017

(54) COMPOSITION FOR PREVENTING AND TREATING ARTHRITIC DISEASES

(75) Inventors: Dong-Suk Park, Seoul (KR); Myung Chul Yoo, Seoul (KR); Do-Young Choi, Gyeonggi-Do (KR); Hyung In Yang, Seoul (KR); Yong-Hyeon Baek, Seoul (KR); Jeong-Eun Huh, Seoul (KR); Kyoung Soo Kim, Seoul (KR); Yong-Baik Cho, Gyeonggi-Do (KR); In Ho Jung, Gyeonggi-Do (KR); Jong Hyun Hur, Gyeonggi-Do (KR); Jae Dong Lee, Seoul (KR)

(73) Assignee: University-Industry Cooperation Group of Kyung Hee University, Gyeonggi-Do (KR)

( * ) Notice: Subject to any disclaimer, the term of this patent is extended or adjusted under 35 U.S.C. 154(b) by 430 days.

(21) Appl. No.: 12/865,995

(22) PCT Filed: Feb. 19, 2009

(86) PCT No.: PCT/KR2009/000797
§ 371 (c)(1),
(2), (4) Date: Aug. 3, 2010

(87) PCT Pub. No.: WO2009/104913
PCT Pub. Date: Aug. 27, 2009

(65) Prior Publication Data
US 2011/0003018 A1 Jan. 6, 2011

(30) Foreign Application Priority Data
Feb. 19, 2008 (KR) .................. 10-2008-0014935
Feb. 16, 2009 (KR) .................. 10-2009-0012642

(51) Int. Cl.
*A61K 36/355* (2006.01)
*A61K 36/8964* (2006.01)
*A23L 33/105* (2016.01)

(52) U.S. Cl.
CPC .......... *A61K 36/355* (2013.01); *A23L 33/105* (2016.08); *A61K 36/8964* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,193,977 B1 * | 2/2001 | Han et al. .................... 424/773 |
| 2003/0143290 A1 * | 7/2003 | Cho et al. .................... 424/728 |
| 2004/0146539 A1 * | 7/2004 | Gupta .......................... 424/401 |

FOREIGN PATENT DOCUMENTS

| | | | |
|---|---|---|---|
| JP | 11236334 A | * | 8/1999 |
| KR | 10-2004-0026170 | | 3/2004 |
| KR | 10-2005-0097857 | | 10/2005 |

OTHER PUBLICATIONS 2014 http://www.kidsgetarthritistoo.org/about-ja/the-basics/who-gets-ja-and-why.php.*
Fernandes "The role of cytokines in osteoarthritis pathophysiology", Biorheology, 39, pp. 237-246, 2002.
Badger et al., J. Pharmacol. Exp. Ther., 290, pp. 587-593,1999.
Search Report for PCT Application No. PCT/KR2009/000797, 2009.
Choi et al., Osteoarthritis Cartilage,10(6), pp. 471-478, 2002.
Chan et al., Osteoarthritis Cartilage,13(5), pp. 387-394, 2005.
Appleton et al., Adv. Pharmacol., 35, pp. 27-28,1996.
Hardingham et al., J. Rheum (Suppl), 43(2), pp. 86-90, 1995.

* cited by examiner

*Primary Examiner* — Terry A McKelvey
*Assistant Examiner* — Catheryne Chen
(74) *Attorney, Agent, or Firm* — Meyertons, Hood, Kivlin, Kowert & Goetzel, P.C.; Mark R. DeLuca

(57) ABSTRACT

In some embodiments, a composition for the treatment and inhibition or prevention of arthritic diseases includes an extract of mixed herbs, the mixed herbs including an active ingredient with *Lonicera japonica* THUNB and *Anemarrhena asphodeloides* BUNGE.

3 Claims, 17 Drawing Sheets

[Fig. 1]
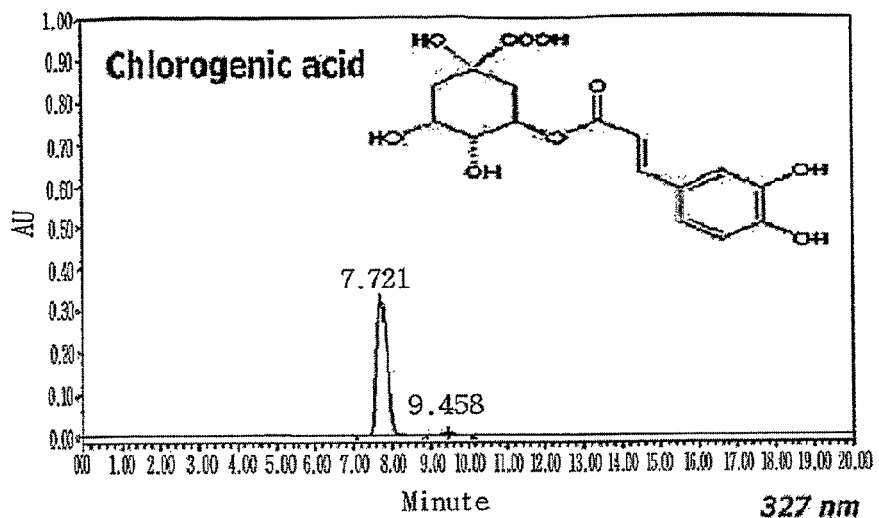
[Fig. 2]
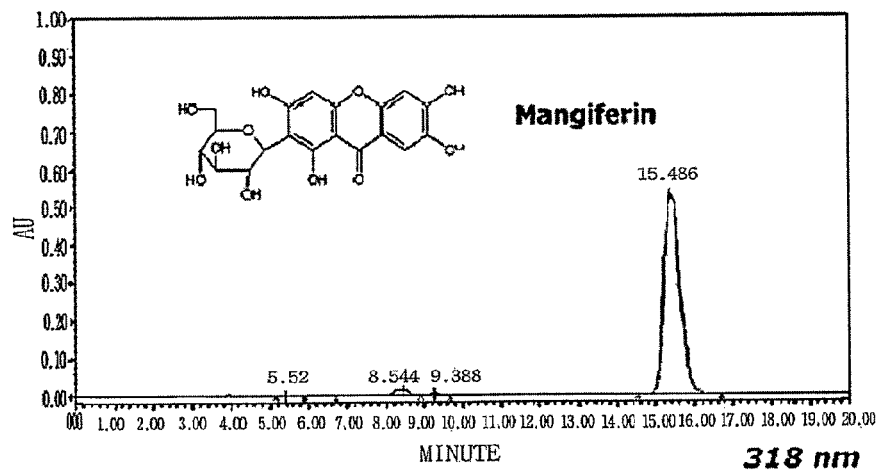
[Fig. 3]
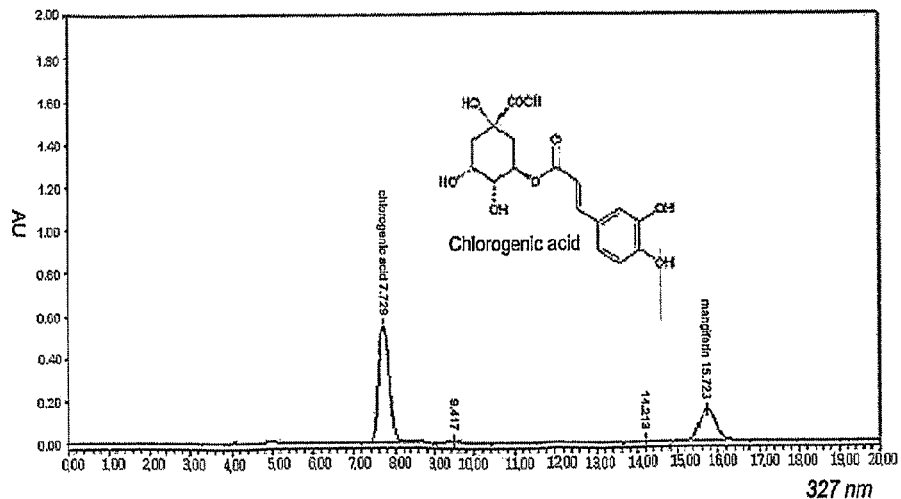

[Fig. 4]
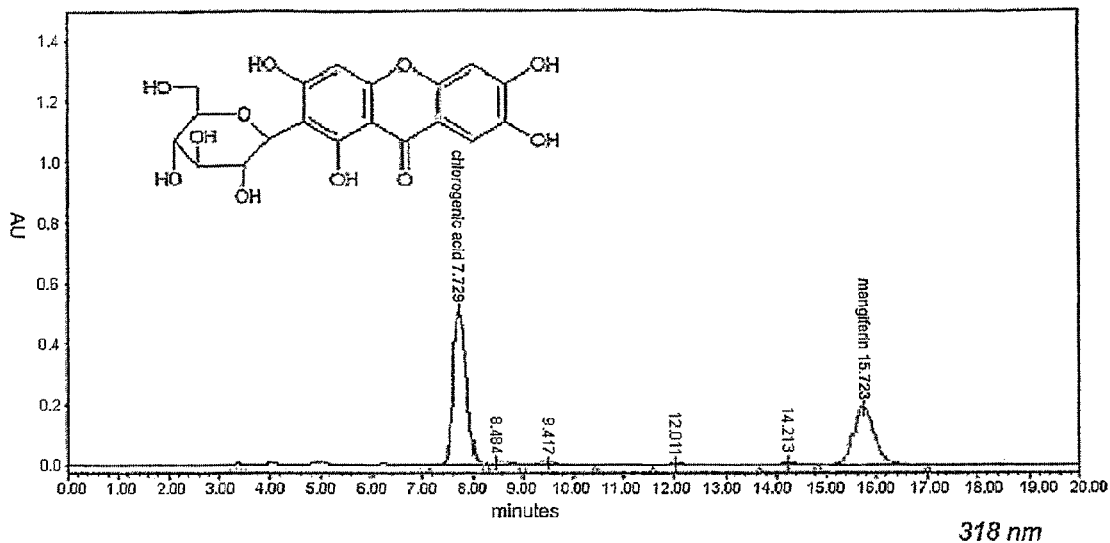
[Fig. 5]
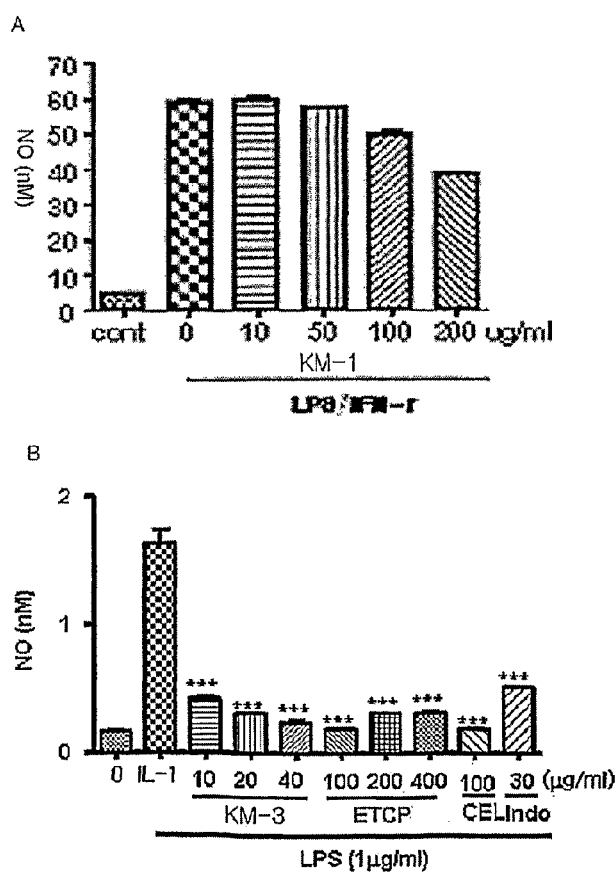

[Fig. 6]
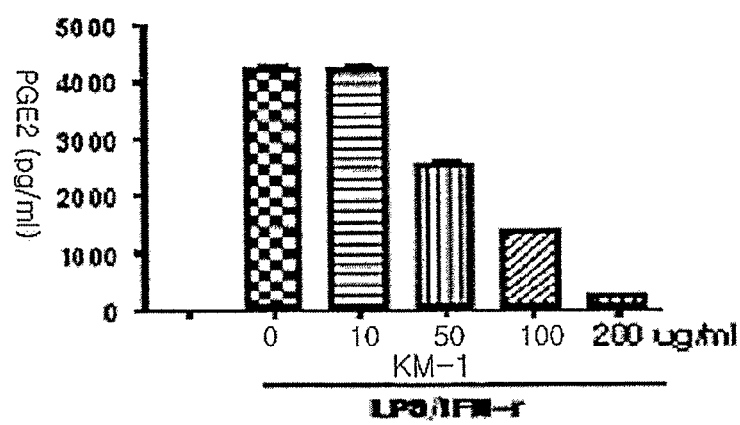
A
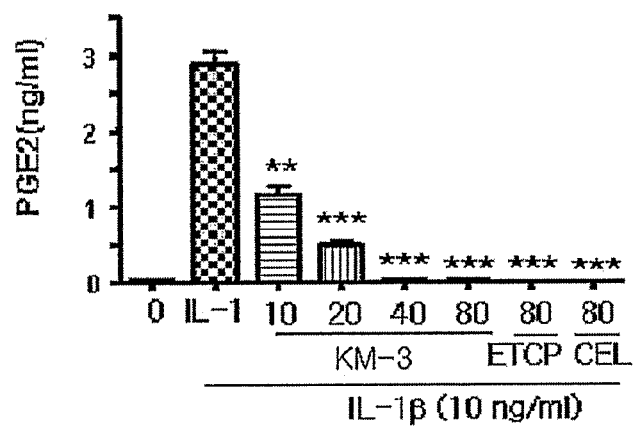
B

[Fig. 7]
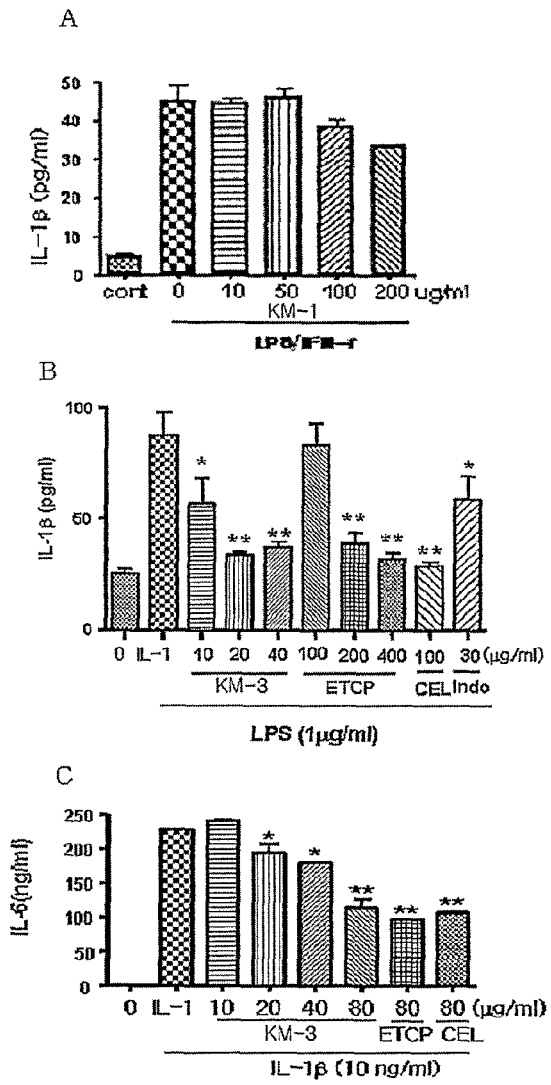
[Fig. 8]
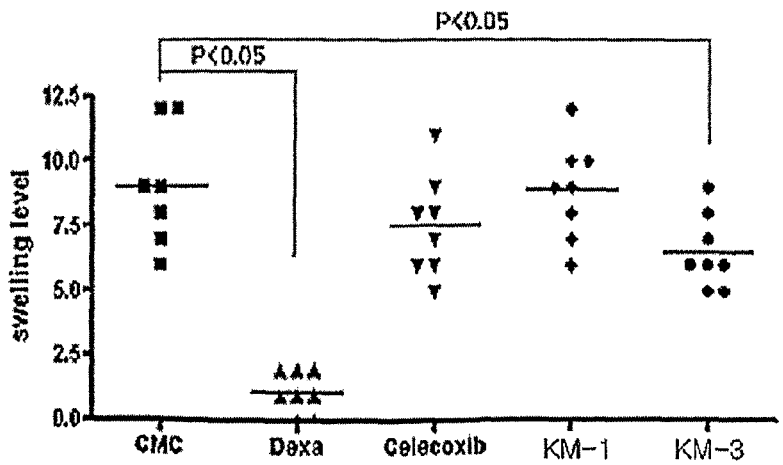

[Fig. 9]
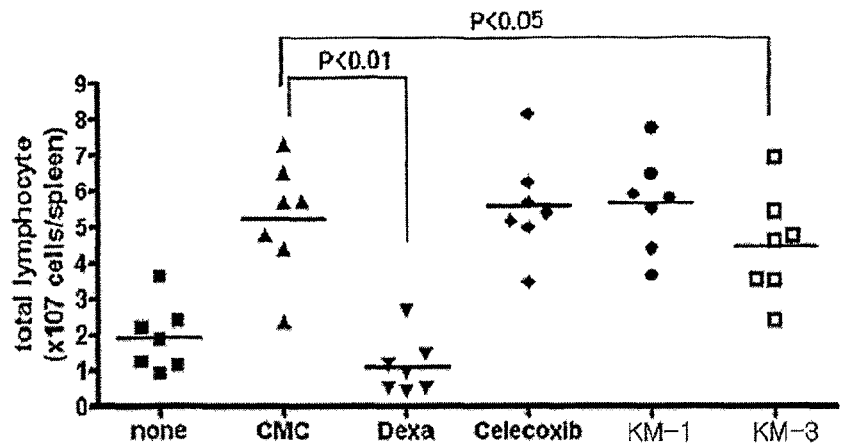
[Fig. 10]
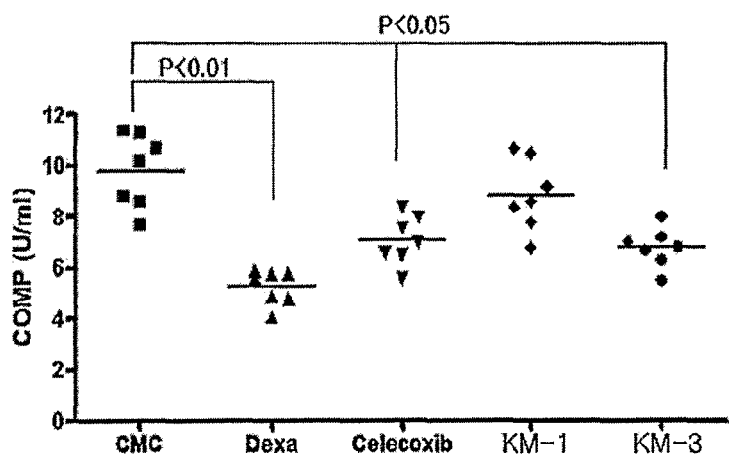
[Fig. 11]
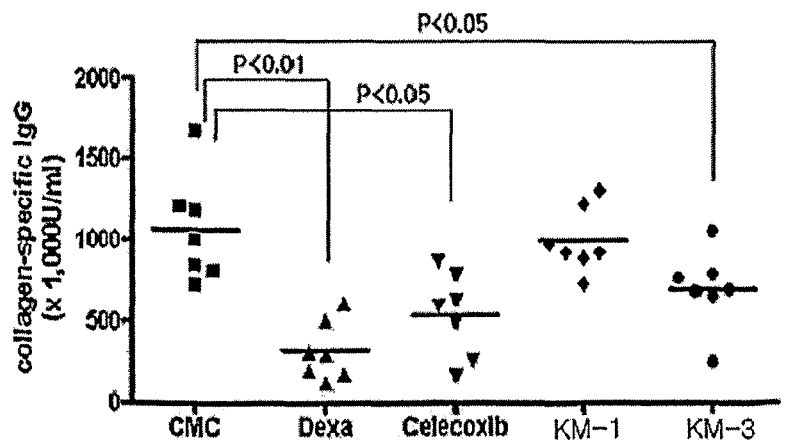

[Fig. 12]
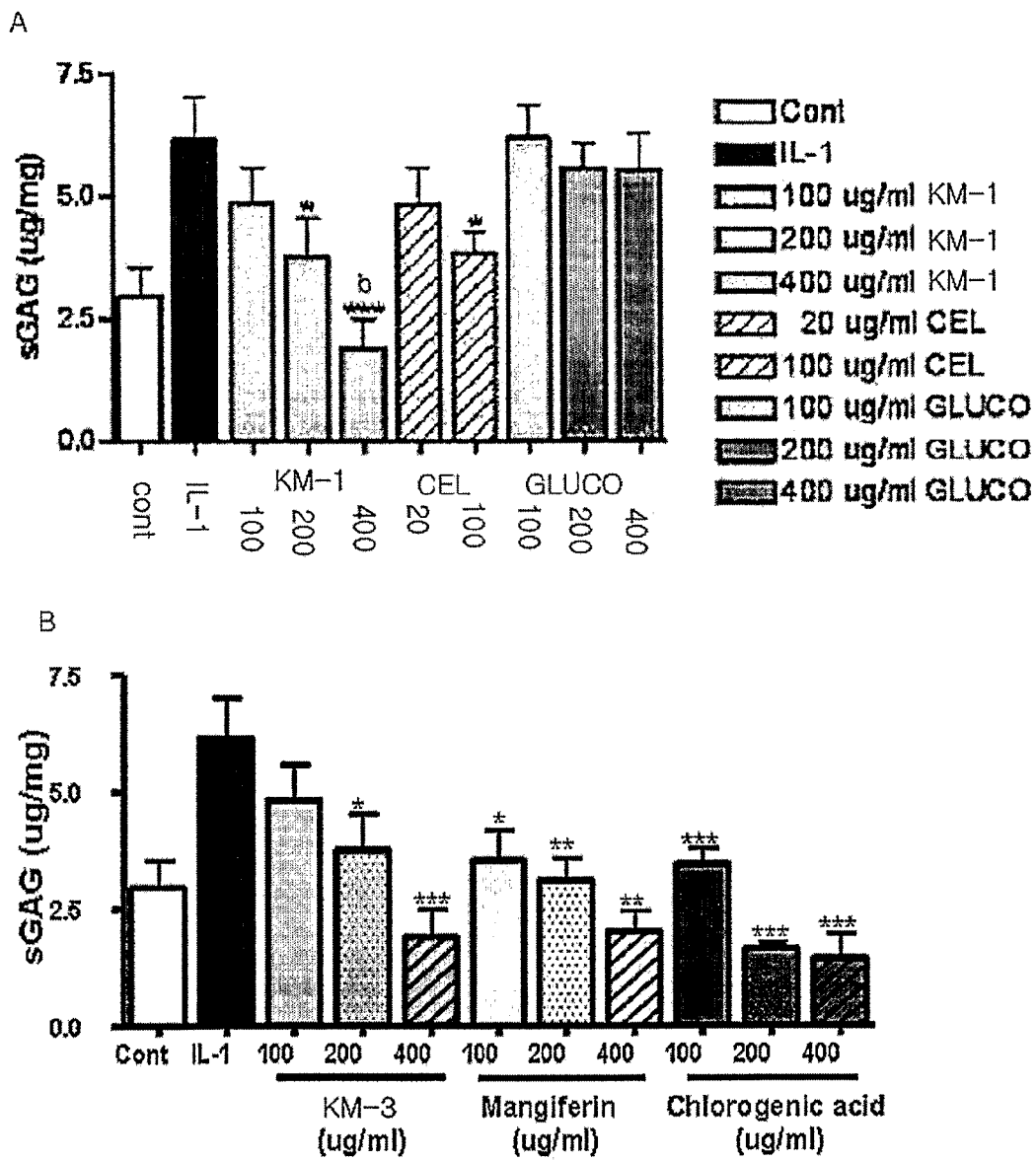

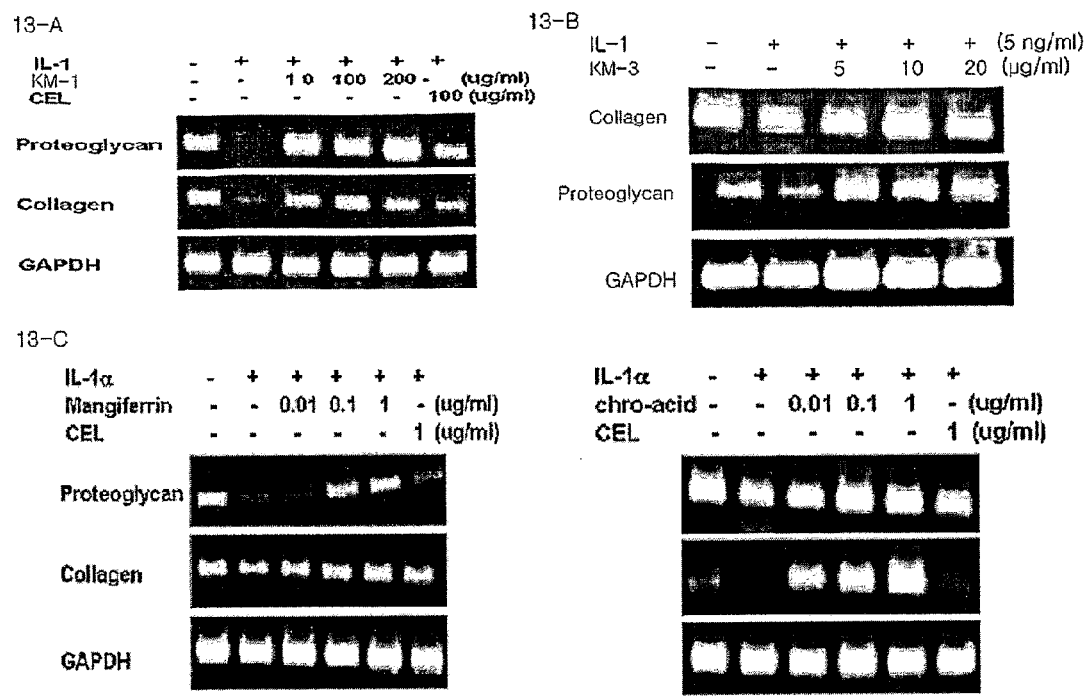

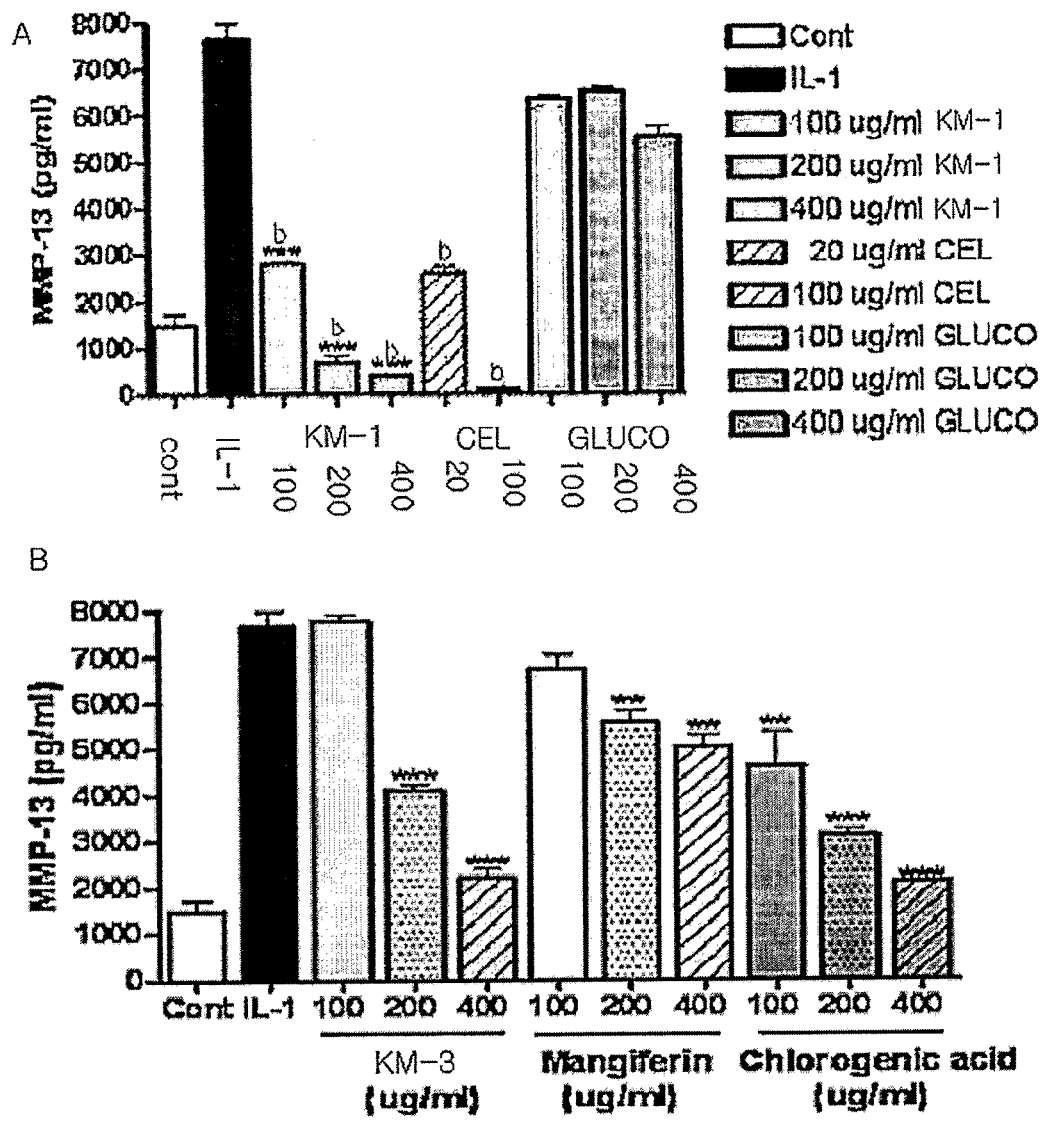
[Fig. 14]

[Fig. 15]
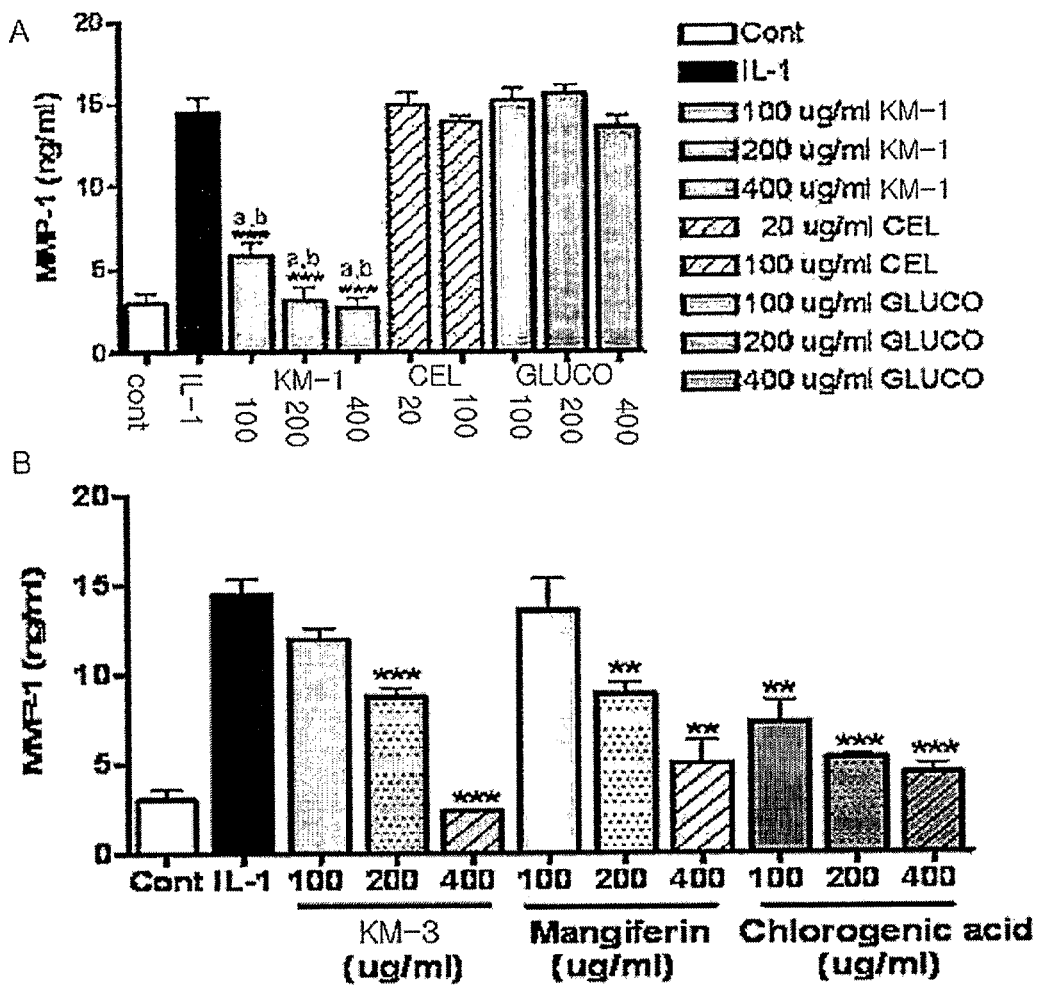

[Fig. 16]
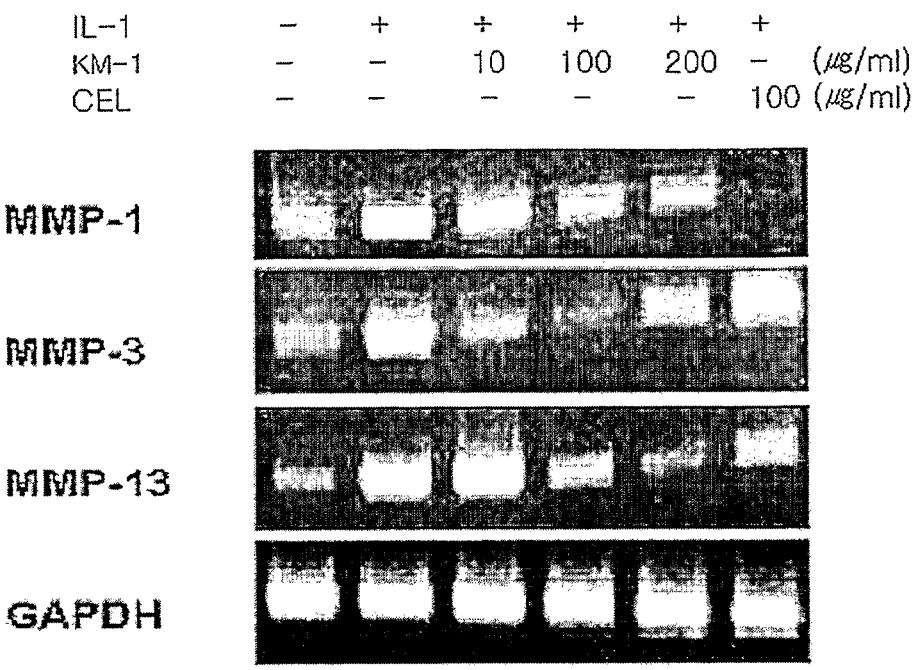
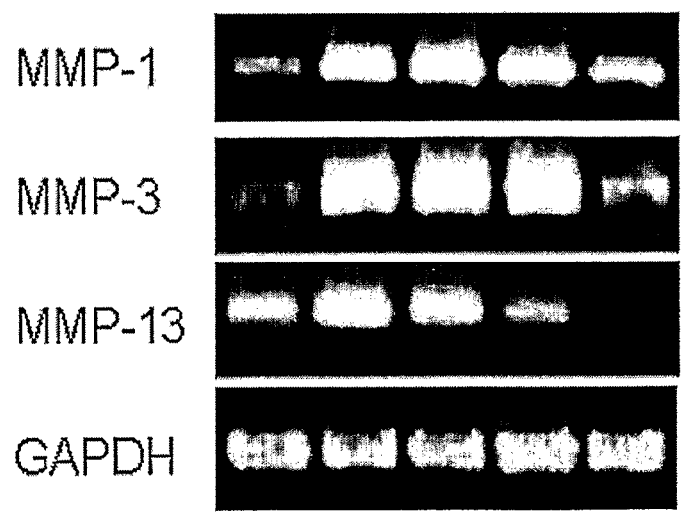

[Fig. 17]
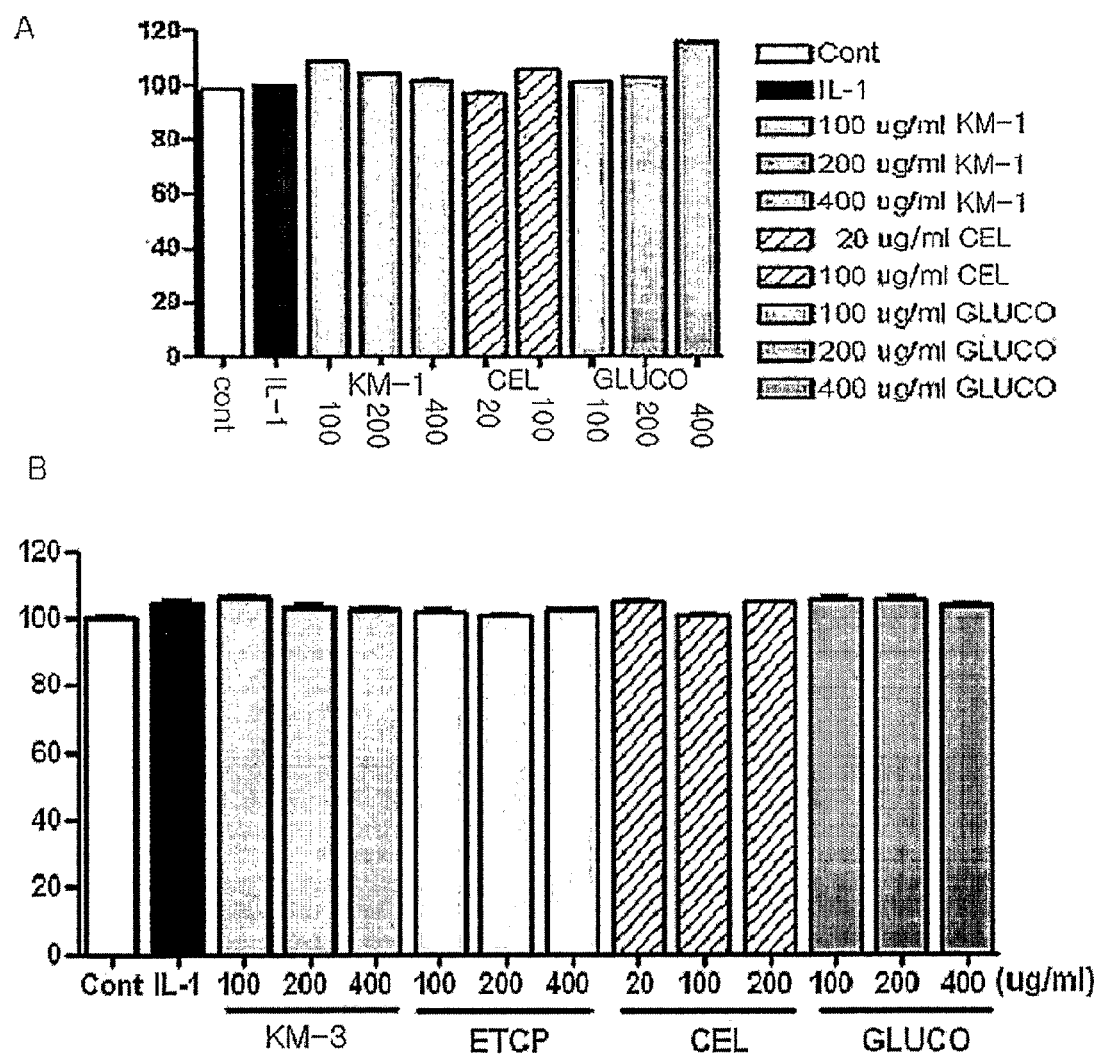

[Fig. 18]
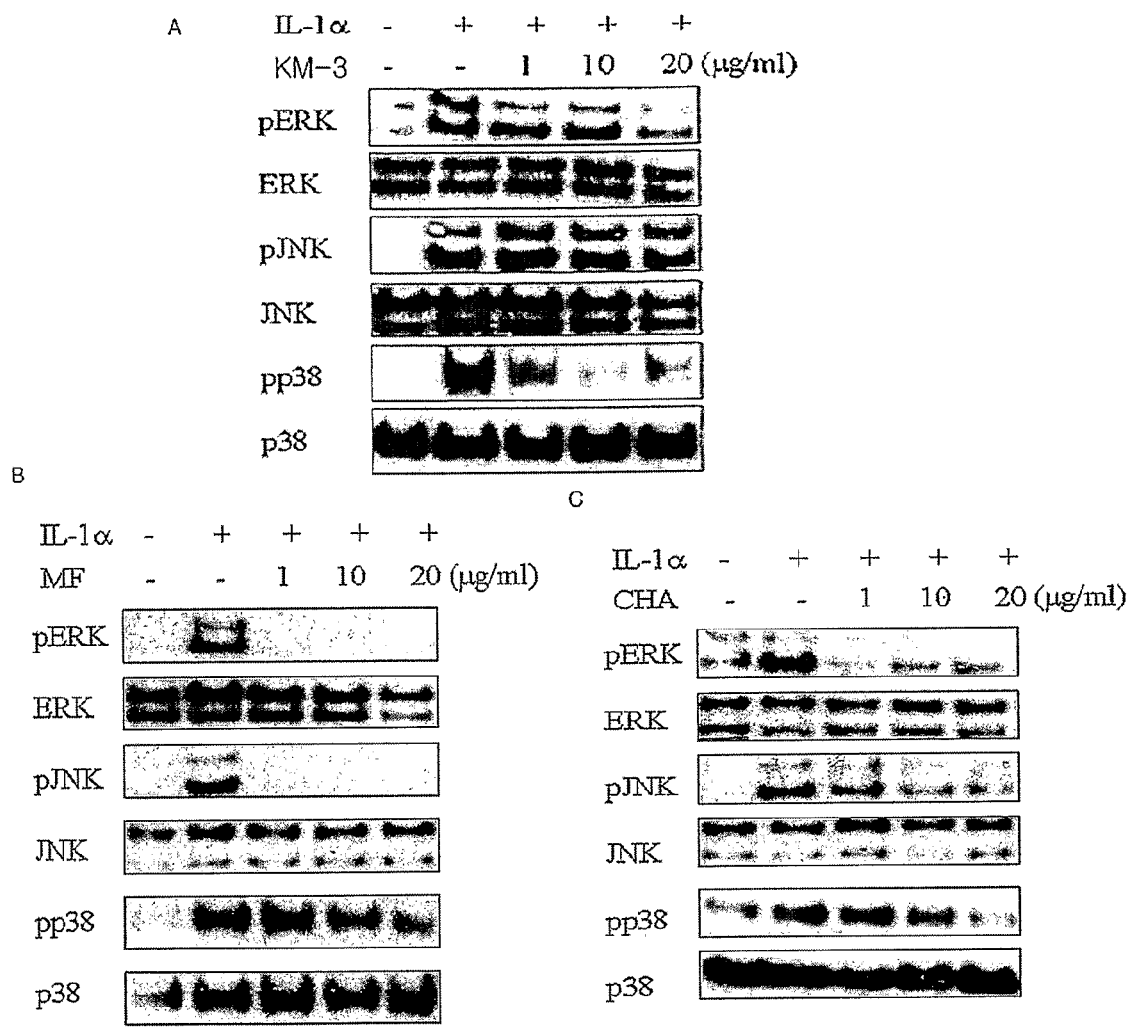

[Fig. 19]
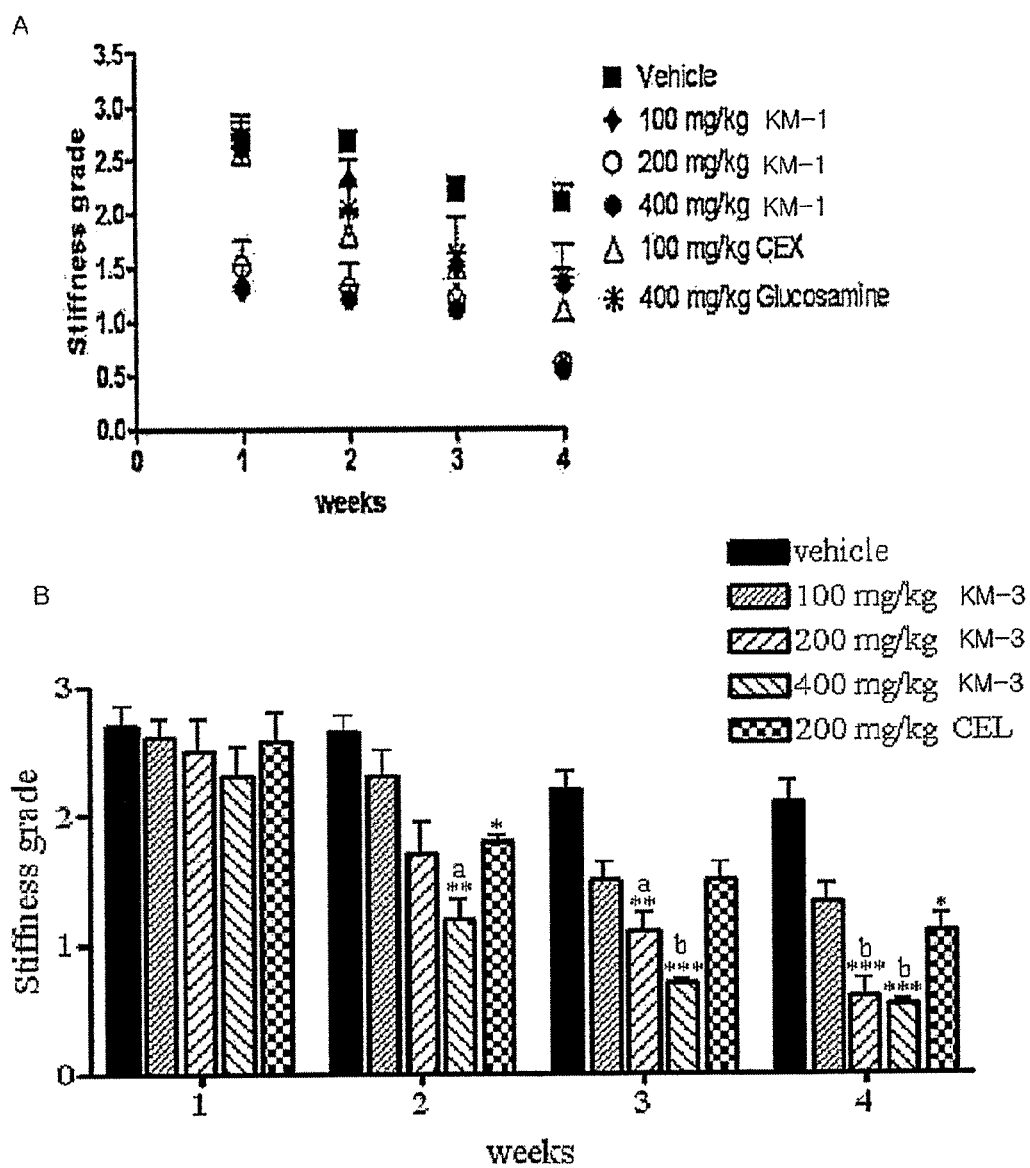

[Fig. 20]
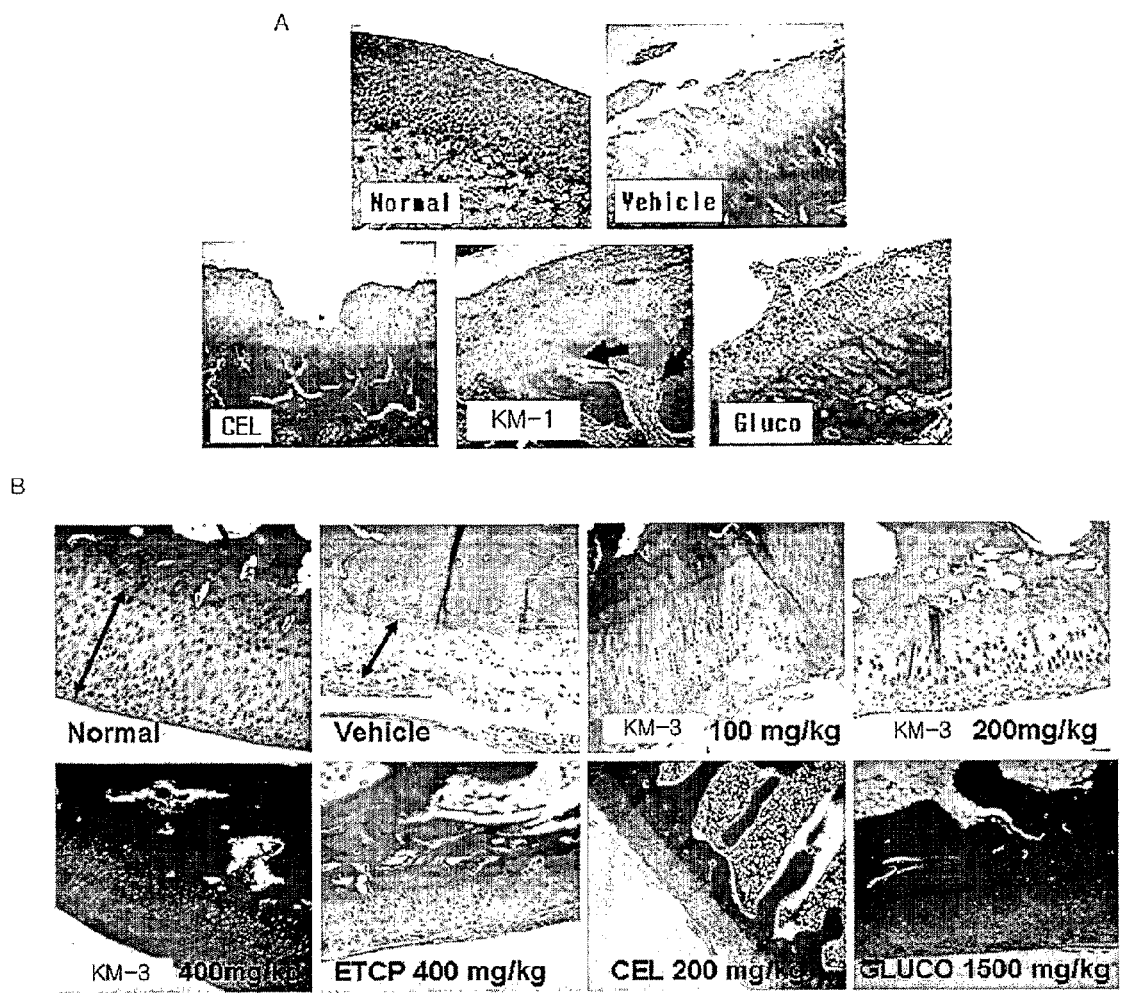

[Fig. 21]
A
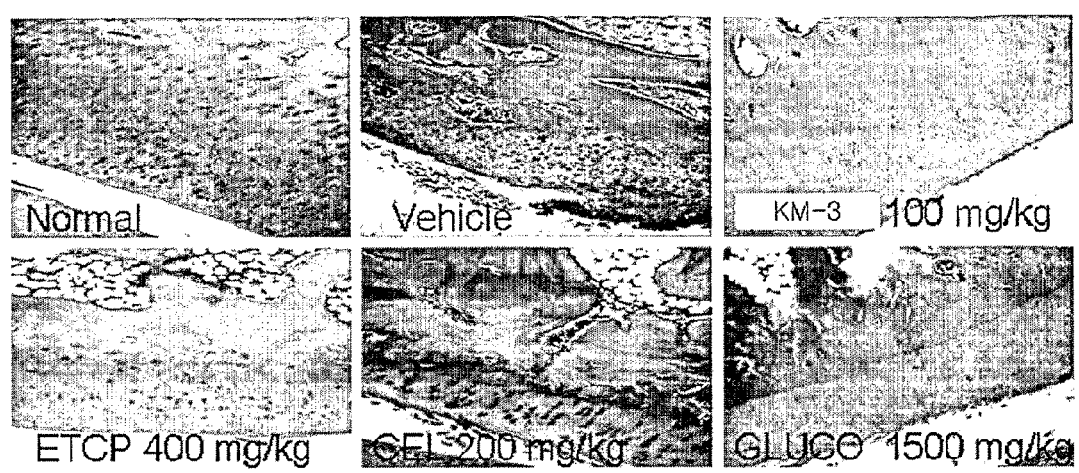
B
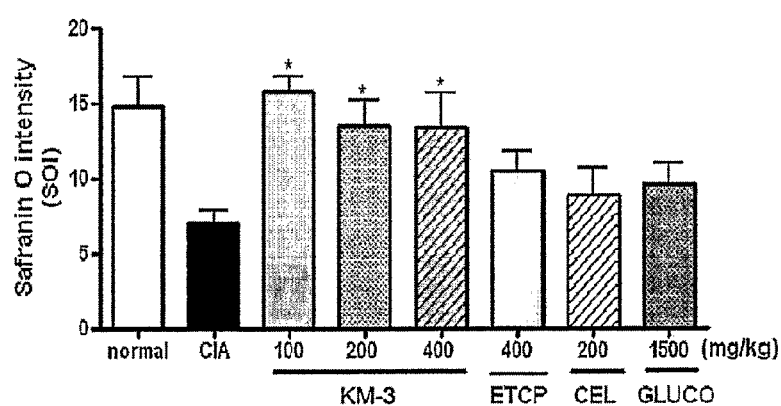

[Fig. 22]
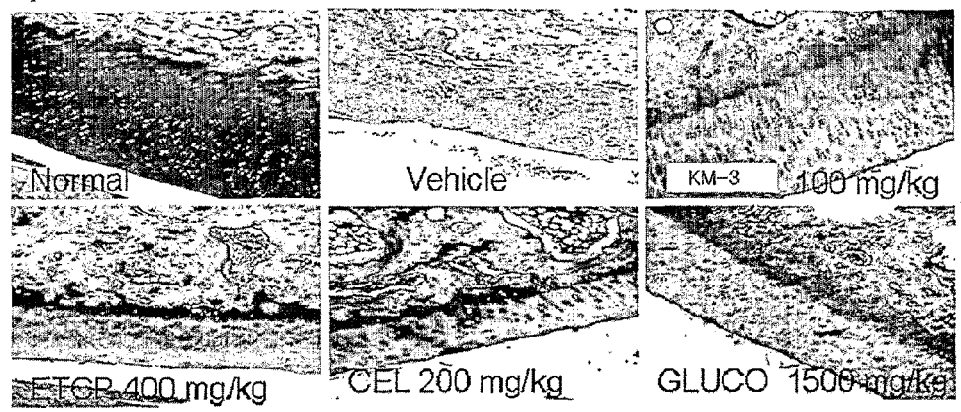
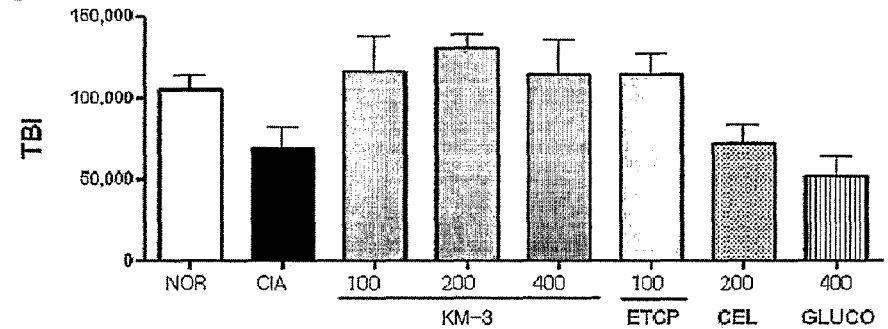
[Fig. 23]
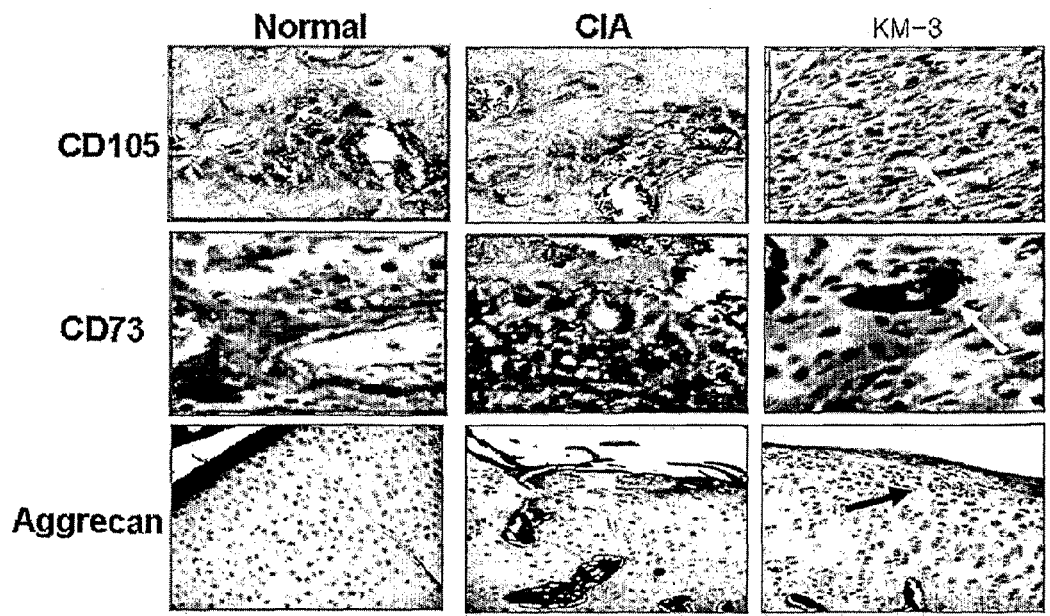

[Fig. 24]
A
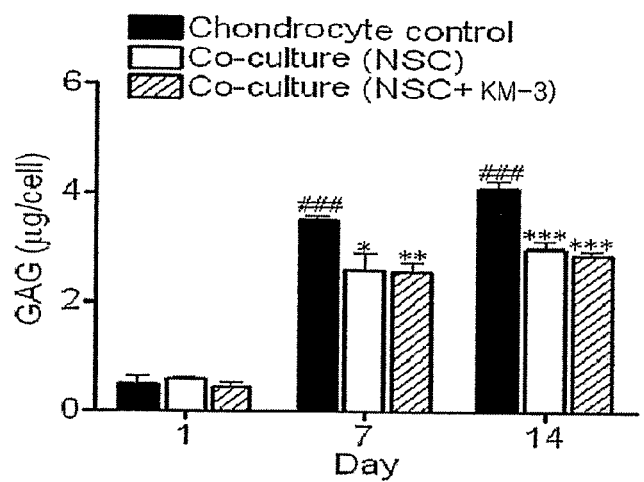
B
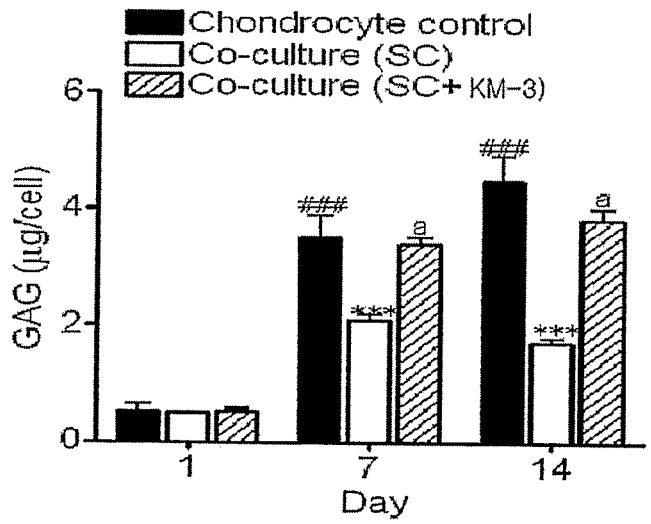

COMPOSITION FOR PREVENTING AND TREATING ARTHRITIC DISEASES

BACKGROUND

1. Field of the Invention

The present invention relates to the field of arthritic disease inhibition or prevention and treatment. In particular, embodiments relate to a composition for the inhibition or prevention and treatment of arthritic disease including an extract of mixed herbs.

2. Description of the Related Art

Arthritis is an autoimmune disease characterized by symptoms such as pain, swelling and stiffness in the joints. The two major forms of arthritis in mammals are inflammatory arthritis such as rheumatoid arthritis (RA), and osteoarthritis (OA), a progressive, degenerative loss of cartilage often secondary to mechanical stress, aging, dysplastic conditions and/or injury. The symptoms of arthritis generally relate to arthrosis of spine, e.g., hallux rigidus, arthrosis psoriaticum, or rheumatic arthritis.

Osteoarthritis manifests similar symptoms to rheumatoid arthritis (RA). In particular, although osteoarthritis begins as a degeneration of articular cartilage, RA begins as an inflammation in synovium. In osteoarthritis, as cartilage deteriorates, a reactive synovitis often develops later on. Conversely, as rheumatoid arthritis erodes cartilage, the secondary osteoarthritis changes the bone and cartilage development. At the final stages of both osteoarthritis and rheumatoid arthritis, suffering joints appear similar to one another.

Osteoarthritis is usually indicated by joint pain which may worsen with exercise and/or an X-ray radiation clearly showing a thinned cartilage. Commonly affected joints are knees, hips, members of the spine, fingers, the base of thumb or the big toe etc. The disease is involved in the destruction of articular cartilage by MMPs (matrix metaloproteinases). MMPs often induce cartilage depletion, which is characterized by degenerative changes in the articular cartilage and caused by the over-production of inflammatory cytokines, e.g., interleukin-1 (IL-1), tumor necrosis factor-$\alpha$(TNF-$\alpha$) etc, causing extremely severe pain in joints, tendons, muscles and ligament (Fernandes J. C., *The role of cytokines in osteoarthritis pathophysiology*, 39, pp 237-246, 2002).

Rheumatoid arthritis (RA) is a common autoimmune disease characterized by the swelling, deformation and destruction of joint, which culminates in severe physical disability. Rheumatic diseases include the diseases occurring at muscles, tendons, joints, bones or sinus, which are generally characterized by an inflammation and/or degeneration. Patients suffering from rheumatoid arthritis may have an imbalance in their immune system, which causes an overproduction of pro-inflammatory cytokines, e.g., TNF-$\alpha$, IL-1 etc. and a lack of anti-inflammatory cytokines, e.g., IL-10, IL-1, etc. RA is characterized by synovial inflammation, which progresses to a cartilage destruction, bone erosion and subsequent joint deformity. During the inflammation process, polymorphonuclear cells, macrophages and lymphocytes are released from the joint. Activated T-lymphocytes produce cytotoxins and pro-inflammatory cytokines, while macrophages stimulate the release of the prostaglandins and cytotoxins. Vasoactive substances such as histamine, kinins and prostaglandins, are released at the site of inflammation and they cause to an edema, erythema and pain at the region of the inflamed joints.

The main pathology of the affected synovial tissue is a hyperplasia and the sub-intimal infiltration of T and B lymphocytes. Synovial tissue hyperplasia forms in pannus tissue, which irreversibly destroys the cartilage and bone in the affected joint. RA progression is associated with elevated levels of TNF-$\alpha$ and IL-1$\beta$ produced by macrophages and dendrite cells, an imbalance of Th1/Th2 and over-production of antigen specific immunoglobulins. More specifically, TNF-$\alpha$ and IL-1$\beta$ directly induce the synthesis of proteolytic enzyme such as matrix metalloproteinase (MMPs) which can break down the extracellular matrix macromolecules. Under normal conditions, the tissue inhibitors of metalloproteinases (TIMPs) bind to MMPs with the ratio of 1:1. The imbalanced ratio of TIMPs to MMPs which is generally caused by the up-regulation of MMPs, results in the continued matrix destruction in RA.

The primary drugs for treating arthritis, which are classified into non-steroidal anti-inflammatory drugs (NSAIDs), include, but are not limited to, aspirin, ibuprofen, naproxen, methotrexate, etc. for alleviating pain and inflammation. Secondary drugs include corticosteroids, slow acting anti-rheumatic drugs (SAARDs) or disease modifying drugs (DMs), e.g., penicilamine, cyclophosphamide, gold salts, azethioprine, levamisole, etc. The first groups of biological-response modifiers (BRMs) approved by FDA for treatment of RA are TNF-$\alpha$ antagonists which plays a role in binding to its receptor or directly binding to the TNF-$\alpha$ protein. However, the use of DMARDs has been impeded by various disadvantages, for example, the potential of its long-term side effects and toxicity, high cost, hypersensitivity to the medications and infections due to TNF-$\alpha$ blockage, etc.

Degenerative arthritis, one of representative osteo-joint diseases is chronic arthritis. It is difficult to treat the disease with conventionally available anti-inflammatory drugs in clinic. Moreover, the drugs give rise to systemic adverse response such as digestive disorder, gastro-intestinal disorder and renal function disorder. Additionally, the adverse response of the drugs occurs more frequently as the age of patient increases, which causes lots of problems in case of long-term systemic treatment in older people. Therefore, due to the shortcomings of previous systemic treatment therapy, a new drug development having an anti-inflammatory effect as well as a protecting and regenerating effect on cartilage has been urgently needed. The recent theory of drug development has been focused on joint tissue lyase inhibitor, free radical scavenger such as SOD, conservation therapy using by long-term treatment of joint tissue components such as chondroitin or glucosamine etc (Badger A. M. et al., *J. Pharmacol. Exp. Ther.*, 290, pp 587-593, 1999; Choi J. H. et al., *Osteoarthritis Cartilage*, 10(6), pp 471-478, 2002).

Various biochemical mechanisms, in particular, nitric oxide synthase (NOS) enzyme generating nitric oxide and the other enzymes involved in the synthesis of prostaglandin (PGs) play an important role in the etiological factor of arthritis in vivo. Accordingly, NOS enzyme generating NO from L-Arginine or cyclooxygenase (COX) involved in the synthesis of various prostaglandins have been the main target to block inflammation of arthritis.

According to recent reports, there are several kinds of NOS enzymes, for example, bNOS (brain NOS) existing in brain, nNOS (neuronal NOS) in neuronal system, eNOS (endothelial NOS) in endothelial system etc, which are expressed at regular levels in the human body. A small amount of NO reproduced thereby plays an important role in maintaining of homeostasis such as neuronal transmission or induction of vasodilation etc. whereas an excess amount of NO occurring abruptly by iNOS (induced NOS) induced by various cytokines or external stimulator gives rise to cell toxicity or inflammatory reaction. Chronic inflammation is correlated with the increased activity of iNOS (Chan P. S. et al., *Osteoarthritis cartilage*, 13(5), pp 387-394, 2005; Appleton I. et al., *Adv. Pharmacol.*, 35, pp 27-28, 1996).

Generally, arthritis occurs due to the late production rate of proteoglycan or collagen in cartilage, which results in loss of cushion function. The articular cartilage consists of water (70~80%) necessary for lubrication and growth, collagen (10~15%), proteoglycan (5~10%) and chondrocyte, wherein proteoglycan has particular structure with core protein attached with several glycosaminoglycan (GAG) (Hardingham et al., *J. Rheum(Suppl)*, 43(2), pp 86-90, 1995).

*Lonicerae Japonicae* is a flower bud part of *Lonicerae* spp. belonging to Caprifoliaceae. They taste sweet, are good for detoxifying, and are traditionally used for treating dysentery, pain and swelling. They have been known to have antiulcer, antibacterial, antiviral, antispasmodic, diuretic, anti-inflammatory and analgesic bioactivities. The main components are luteolin, inositol, saponin, tannin, isochlorogenic acid, chlorogenic acid etc (B. S. Chung et al., HyangYakDaeSaJeon, Youngrimsa, pp 939-940, 1989).

*Anemarrhena asphodeloides* BUNGE belongs to Haemodoraceae. They taste sour and are traditionally used to treat fever, dire thirst, cough and diabetes. They have been known to have hypoglycaemic, anti-pyretic, antiplatelet aggregation, inhibits stress ulcer, sedative, inhibits cAMP phosphodiesterase and Na/K-ATPase, haemolytic, antitumour bioactivities. The main components are various saponins such as timosaponin A-I, timosaponin A-II, timosaponin A-III, timosaponin A-IV, timosaponin B-I, and timosaponin nicotinic acid, magniferin, isomangiferin etc (B. S. Chung et al., HyangYakDaeSaJeon, Youngrimsa, pp 203-204, 1989).

However, the therapeutic effect of an extract of mixed herbs with *Lonicera japonica* THUNB and *Anemarrhena asphodeloides* BUNGE on the arthritic disease has not been reported or disclosed in any of above cited literatures, the disclosures of which are incorporated herein by reference.

SUMMARY

In some embodiments, a composition for the inhibition or prevention and treatment of arthritic disease includes an extract of mixed herbs with *Lonicera japonica* THUNB and *Anemarrhena asphodeloides* BUNGE.

In some embodiments, a pharmaceutical composition including an extract of mixed herbs with *Lonicera japonica* THUNB and *Anemarrhena asphodeloides* BUNGE as an active ingredient is provided for the treatment and inhibition or prevention of arthritic diseases, in particular, by way of stimulating the recovery of cartilage tissue, protecting cartilage damage due to the stimulation of cartilage component and inhibition of cartilage dissociation, and inhibiting inflammation and pain.

In some embodiments, an extract includes the crude extract soluble in water, $C_1$ to $C_4$ lower alcohol, and the mixtures thereof; and the butanol soluble extract obtained by fractionation with butanol solution therefrom.

In some embodiments, mixed herbs with *Lonicera japonica* THUNB and *Anemarrhena asphodeloides* BUNGE are provided with a mixed ratio ranging from 0.5~3:1 by weight (w/w %). In various embodiments, the mixed ratio ranges from 1~2:1 by weight (w/w %). In certain embodiments, the mixed ratio ranges from 1.5~2:1 by weight (w/w %).

In some embodiments, the extract includes chlorogenic acid as a standard component in the extract of *Lonicera japonica* THUNB and mangiferin as a standard component in the extract of *Anemarrhena asphodeloides* BUNGE. In several embodiments, the extract includes 0.5~6 (w/w %) chlorogenic acid and 0.5~4 (w/w %) mangiferin as a standard component in total extract. In various embodiments, the extract includes 1.5~5 (w/w %) chlorogenic acid and 0.5~3.5 (w/w %) mangiferin as a standard component in total extract. In certain embodiments, the extract includes 3~4.5 (w/w %) chlorogenic acid and 0.5~2.5 (w/w %) mangiferin as a standard component in total extract.

The term "arthritic disease" disclosed herein includes degenerative arthritis, rheumatic arthritis or Lupus arthritis, preferably, rheumatic arthritis.

In some embodiments, an extract of mixed herbs with *Lonicera japonica* THUNB and *Anemarrhena asphodeloides* BUNGE is used for the preparation of therapeutic agent for the treatment and inhibition or prevention of arthritic disease in mammal or human.

In some embodiments, a method of treating or preventing arthritic disease in human or mammal includes administering a therapeutically effective amount of an extract of mixed herbs with *Lonicera japonica* THUNB and *Anemarrhena asphodeloides* BUNGE, as an effective ingredient, together with a pharmaceutically acceptable carrier thereof.

An extract of mixed herbs with *Lonicera japonica* THUNB and *Anemarrhena asphodeloides* BUNGE may be used for the preparation of a therapeutic agent for the treatment and inhibition or prevention of arthritic disease in mammal or human. Additionally, an extract of mixed herbs with *Lonicera japonica* THUNB and *Anemarrhena asphodeloides* BUNGE may be used as an active ingredient and a pharmaceutically acceptable carrier thereof for treating and preventing arthritic disease.

For example, in some embodiments, *Lonicera japonica* THUNB and *Anemarrhena asphodeloides* BUNGE are dried, cut, crushed, mixed together and added to approximately 1 to 20-fold (or 5 to 10-fold in certain embodiments) volume of distilled water, $C_1$ to $C_4$ lower alcohols or the mixtures thereof, the mixing ratio of the water and alcohol may be approximately 1:0.1 to 1:10 (v/v) (or 1:0.5 to 1:5 (v/v) in certain embodiments); the solution is treated with hot water at the temperature ranging from 10° C.~100° C. (or 60° C.~100° C. in certain embodiments) for a period ranging from 1 to 6 hours (or 2 to 4 hours in certain embodiments); the extraction method may include, extraction with hot water, cold water, reflux extraction, or ultrasonication extraction; the extract is collected with filtration, concentrated under reduced pressure and dried to obtain a crude extract.

In some embodiments, the equivalent of butanol soluble solution is added to the above-mentioned crude extract, and then the suspension is performed to fractionation to obtain a purified extract.

In some embodiments, the crude extract and purified extract prepared by the above-described procedures includes chlorogenic acid as a standard component in the extract of *Lonicera japonica* THUNB and mangiferin as a standard component in the extract of *Anemarrhena asphodeloides* BUNGE. In several embodiments, the extract includes 0.5~6 (w/w %) chlorogenic acid and 0.5~4 (w/w %) mangiferin as a standard component in total extract. In various embodiments, the extract includes 1.5~5 (w/w %) chlorogenic acid and 0.5~3.5 (w/w %) mangiferin as a standard component in total extract. In certain embodiments, the extract includes 3~4.5 (w/w %) chlorogenic acid and 0.5~2.5 (w/w %) mangiferin as a standard component in total extract.

Additionally, in some embodiments, the above-described procedures include a further step to fractionate or isolate more potent fractions or compounds by conventional procedure well-known in the art, for example, the procedure disclosed in the literature (Harborne J. B. Phytochemical methods: *A guide to modern techniques of plant analysis*, 3$^{rd}$ Ed. ppb-7, 1998).

In some embodiments, a method of treating or preventing arthritic disease in human or mammal includes administering a therapeutically effective amount of an extract of mixed herbs with *Lonicera japonica* THUNB and *Anemarrhena asphodeloides* BUNGE as an effective ingredient, together with a pharmaceutically acceptable carrier thereof.

In some embodiments, the composition for treating and preventing arthritic diseases may include the above-described extract as 0.1~50% by weight based on the total weight of the composition.

In some embodiments, the composition may further include conventional carrier adjuvants or diluents in accordance with a method well known in the art. It is preferable that the carrier is used as an appropriate substance according to the usage and application method, but it is not limited. Appropriate diluents are listed in the written text of Remington's Pharmaceutical Science (Mack Publishing co, Easton Pa.).

In some embodiments, the composition may be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and/or mineral oil. The formulations may additionally include fillers, anti-agglutinating agents, lubricating agents, wetting agents, flavoring agents, emulsifiers, preservatives and the like. In certain embodiments, composition may be formulated so as to provide quick, sustained or delayed release of the active ingredient after their administration to a patient by employing any of the procedures well known in the art.

For example, the composition may be dissolved in oils, propylene glycol or other solvents that are commonly used to produce an injection. Suitable examples of the carriers include, but are not limited to, physiological saline, polyethylene glycol, ethanol, vegetable oils, and isopropyl myristate. For topical administration, the extract may be formulated in the form of ointments and creams.

Pharmaceutical formulations containing the composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition in pharmaceutical dosage forms may be used in the form of their pharmaceutically acceptable salts, and also may be used alone or in appropriate association, as well as in combination with other pharmaceutically active compounds.

In some embodiments the extract or composition is administered at an amount ranging from 0.1 to 1000 mg/kg by weight/day. In certain embodiments, the extract or composition is administered at an amount ranging from 1 to 100 mg/kg by weight/day. The desirable dose of the extract or composition may vary, however, according to the condition and the weight of the subject, severity, drug form, route and period of administration, and may be chosen by those skilled in the art. The dose may be administered in single or divided into several times per day.

The pharmaceutical composition may be administered to a subject animal such as mammals (rat, mouse, domestic animals or human) via various routes. All modes of administration are contemplated, for example, administration may be made orally, rectally or by intravenous, intramuscular, subcutaneous, intra-cutaneous, intrathecal, epidural or intracerebroventricular injection.

In some embodiments, a functional health food includes an extract of mixed herbs with *Lonicera japonica* THUNB and *Anemarrhena asphodeloides* BUNGE.

The term "functional health food" defined herein refers to "a functional food having enhanced functionality such as physical functionality or physiological functionality, in which the enhanced functionality is attained by adding the extract to conventional food to prevent or improve an aimed disease in human or mammal".

In some embodiments, a health care food includes the extract, together with a sitologically acceptable additive for the inhibition or prevention and alleviation of aimed disease.

The term "health care food" defined herein refers to "a food containing the extract having no specific or selected shape or size, but generally intended to be produced, in a relatively small amount of quantity, as a form of additive or, in a relatively large amount of quantity, as a form of capsule, pill, tablet etc".

The term "sitologically acceptable additive" defined herein refers to "any substance the intended use of which results or may reasonably be expected to result—directly or indirectly—in its becoming a component or otherwise affecting the characteristics of any food" for example, a thickening agent, maturing agent, bleaching agent, sequesterants, humectant, anticaking agent, clarifying agents, curing agent, emulsifier, stabilizer, thickner, bases and acid, foaming agents, nutrients, coloring agent, flavoring agent, sweetner, preservative agent, antioxidant, etc, which are well-known in the art.

If a substance is added to a food for a specific purpose in that food, it is referred to as a direct additive and indirect food additives are those that become part of the food in trace amounts due to its packaging, storage or other handling.

Health foods can be contained in food, health beverages, dietary therapy etc, and may be used as a form of powder, granule, tablet, chewing tablet, capsule, beverage etc for preventing or improving an aimed disease.

In some embodiments, the extract may be added to food or beverages for inhibition or prevention and improvement of an aimed disease. The amount of the extract in the food or beverage as a functional health food or health care food may generally range from about 0.01 to 15 w/w % of total weight of food. In some embodiments, the extract is used as an additive in the amount ranging from about 0.01 to 5% in food such as noodles and the like, and from 40 to 100% in health care food on the ratio of 100% of the food composition. The amount of the extract in the functional health food, health care food or special nutrient food, however, may be varied in accordance to the intended purpose of each food.

In such embodiments where the health beverage composition contains the extract as an essential component in the indicated ratio, there is may be no particular limitation on the other liquid component. The other component may be various deodorants or natural carbohydrates etc such as are contained in conventional beverages. Examples of the aforementioned natural carbohydrates are monosaccharide such as glucose, fructose etc; disaccharide such as maltose, sucrose etc; conventional sugar such as dextrin, cyclodextrin; and sugar alcohol such as xylitol, and erythritol etc.

Examples of the aforementioned deodorants are natural deodorants such as taumatin, stevia extract such as levaudioside A, glycyrrhizin et al., and synthetic deodorant such as saccharin, aspartam et al.; such deodorants may be used favorably. In some embodiments, the amount of natural carbohydrate ranges from about 1 to 20 g in the ratio of 100 ml of present beverage composition. In certain embodiments, the amount of natural carbohydrate ranges from about 5 to 12 g in the ratio of 100 ml of present beverage composition.

Other components of the composition may include various nutrients, a vitamins, minerals or electrolytes, synthetic flavoring agents, coloring agents and improving agents in case of cheese, chocolate et al., pectic acid and the salt thereof, alginic acid and the salt thereof, organic acid, protective colloidal adhesive, pH controlling agents, stabilizers, preservatives, glycerin, alcohol, carbonizing agents used in carbonate beverage etc. Other components of the composition may also include fruit juice for preparing natural fruit juice, fruit juice beverage and vegetable beverage; the components may be used independently or in combination. The ratio of the components may not be critical, however, in some embodiments, the ratio generally ranges from about 0 to 20 w/w % per 100 w/w % of the composition. Examples of addable food including aforementioned extract therein are various food, beverage, gum, vitamin complex, health improving food and the like.

It will be apparent to those skilled in the art that various modifications and variations can be made in the compositions, use and preparations described herein without departing from the spirit or scope of the invention.

An extract or composition of mixed herbs with *Lonicera japonica* THUNB and *Anemarrhena asphodeloides* BUNGE may advantageously demonstrate a potent anti-inflammatory effect through various experiments, i.e., the inhibitory effect on the dissociation of proteoglycan and type II collagen in cartilage tissue; protecting effect on cartilage due to the inhibition of MMP-1, MMP-3 and MMP-13 activity; and the restoring effect on cartilage tissue; the anti-inflammatory and antiphlogistic effect in edema animal model; anti-inflammatory effect confirmed by the inhibition test on $PEG_2$ activity, GAG degradation and genetic toxicity tests, therefore, it can be used as the effective and safe therapeutics or health food for treating and preventing arthritic disease.

BRIEF DESCRIPTION OF THE DRAWINGS

The present invention will be better understood and other advantages will appear on reading the detailed description of some embodiments taken as non-limiting examples and illustrated by the following drawings in which:

FIG. 1 is a chart illustrating the result of chromatogram analysis on chlorogenic acid, a standard component contained in the extract of *Lonicera japonica* THUNB;

FIG. 2 is a chart illustrating the result of chromatogram analysis on mangiferin, a standard component contained in the extract of *Anemarrhena asphodeloides* BUNGE;

FIG. 3 is a chart illustrating the result of chromatogram analysis on chlorogenic acid, a standard component in KM-3;

FIG. 4 is a chart illustrating the result of chromatogram analysis on mangiferin, a standard component in KM-3;

FIG. 5-A is a chart illustrating the inhibitory effect on NO production by treatment of KM-1;

FIG. 5-B is a chart illustrating the inhibitory effect on NO production by treatment of KM-3;

FIG. 6-A is a chart illustrating the inhibitory effect on $PGE_2$ production by treatment of KM-1;

FIG. 6-B is a chart illustrating the inhibitory effect on $PGE_2$ production by treatment of KM-3;

FIG. 7-A is a chart illustrating the inhibitory effect on IL-1β production by treatment of KM-1;

FIG. 7-B is a chart illustrating the inhibitory effect on IL-1β production by treatment of KM-3;

FIG. 7-C is a chart illustrating the inhibitory effect on IL-6 production by treatment of KM-3;

FIG. 8 is a chart illustrating the inhibitory effects of KM-1 and KM-3 on swelling of Collagenase-Induced Osteoarthritis (CIA) animal model;

FIG. 9 is a chart illustrating the inhibitory effects of KM-1 and KM-3 on the number of increased lymphocytes in the Collagenase-Induced Osteoarthritis (CIA) animal model;

FIG. 10 is a chart illustrating the inhibitory effect of KM-1 and KM-3 on the cartilage erosion in the Collagenase-Induced Osteoarthritis (CIA) animal model;

FIG. 11 is a chart illustrating the inhibitory effect of KM-1 and KM-3 on the production of collagen-specific IgG antibody in the Collagenase-Induced Osteoarthritis (CIA) animal model test;

FIG. 12-A is a chart illustrating the inhibitory effect of KM-1 on the degradation of proteoglycan;

FIG. 12-B is a chart illustrating the inhibitory effects of KM-3, mangiferin and chlorogenic acid on the degradation of proteoglycan;

FIG. 13-A is a chart illustrating the increased mRNA gene expression of proteoglycan and type II collagen in cartilage tissue of the patient suffering from osteoarthritis, treated with KM-1 by RT-PCR method;

FIG. 13-B is a chart illustrating the increased mRNA gene expression of proteoglycan and type II collagen in cartilage tissue of the patient suffering from osteoarthritis, treated with KM-3 by RT-PCR method;

FIG. 13-C is a chart illustrating the increased mRNA gene expression of proteoglycan and type II collagen in cartilage tissue of the patient suffering from osteoarthritis, treated with mangiferin and chlorogenic acid by RT-PCR method;

FIG. 14-A is a chart illustrating the inhibitory effect of KM-1 on the level of MMP-13 activity in cartilage tissue of the patient suffering from osteoarthritis;

FIG. 14-B is a chart illustrating the inhibitory effect of KM-3 on the level of MMP-13 activity in cartilage tissue of the patient suffering from osteoarthritis;

FIG. 15-A is a chart illustrating the inhibitory effect of KM-1 on the level of MMP-1 activity in cartilage tissue of the patient suffering from osteoarthritis;

FIG. 15-B is a chart illustrating the inhibitory effect of KM-3, mangiferin and chlorogenic acid on the level of MMP-1 activity in cartilage tissue of the patient suffering from osteoarthritis;

FIG. 16 is a chart illustrating the inhibitory effect on the level of mRNA gene expression of MMP-1, MMP-3 and MMP-13 of cartilage tissue of the patient from osteoarthritis treated with KM-1 (A) and KM-3 (B);

FIG. 17 is a chart illustrating the determination of the cytotoxicity of cartilage tissue of the patient suffering from osteoarthritis treated with KM-1 (A) and KM-3 (B);

FIG. 18-A is a chart illustrating the inhibitory effect on the phosphorylation of several mitogen activated protein kinase (MAPK) by KM-3 was involved in the cartilage protection of osteoarthritis cartilage;

FIG. 18-B is a chart illustrating the inhibitory effect on the phosphorylation of several mitogen activated protein kinase (MAPK) by mangiferin was involved in the cartilage protection of osteoarthritis cartilage;

FIG. 18-C is a chart illustrating the inhibitory effect on the phosphorylation of several mitogen activated protein kinase (MAPK) by chlorogenic acid was involved in the cartilage protection of osteoarthritis cartilage;

FIG. 19 is a chart illustrating the swelling and mobility recovery effect of KM-1 (A) and KM-3 (B) of joint in Collagenase-Induced Osteoarthritis (CIA) animal model;

FIG. 20-A is a depiction of the cartilage protective effect of KM-1 by morphological analysis in joint of Collagenase-Induced Osteoarthritis (CIA) animal model;

FIG. 20-B is a depiction of the cartilage protective effect of KM-3 by morphological analysis in joint of Collagenase-Induced Osteoarthritis (CIA) animal model;

FIG. 21-A is a depiction of the recovery effect of KM-1 on proteoglycan expression by Safranin O staining analysis in joint of Collagenase-Induced Osteoarthritis (CIA) animal model;

FIG. 21-B is a chart illustrating the recovery effect of KM-3 on proteoglycan expression by Safranin O staining analysis in joint of Collagenase-Induced Osteoarthritis (CIA) animal model;

FIG. 22-A is a depiction of the recovery effect of KM-1 on collagen expression by Masson Trichrome staining analysis in joint of Collagenase-Induced Osteoarthritis (CIA) animal model;

FIG. 22-B is a chart illustrating the recovery effect of KM-3 on collagen expression by Masson Trichrome staining analysis in joint of Collagenase-Induced Osteoarthritis (CIA) animal model;

FIG. 23 is a depiction of the cartilage regenerating effect of KM-3 on the expression of differentiated mesenchymal stem cells (CD105, CD73) from the tissue of subchondral bone and aggrecan in joint of Collagenase-Induced Osteoarthritis (CIA) animal model;

FIG. 24-A is a chart illustrating the inhibitory effect of KM-3 on the GAG degradation test performed by co-culturing the cartilage cell and the subchondral bone tissue at the normal region (NSC) isolated from the cartilage tissue and subchondral bone of patients suffering from osteoarthritis;

FIG. 24-B is a chart illustrating the inhibitory effect of KM-3 on the GAG degradation test performed by co-culturing the cartilage cell and the subchondral bone tissue at the abnormal region (SC) isolated from the cartilage tissue and subchondral bone of patients suffering from osteoarthritis.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF ILLUSTRATIVE EMBODIMENTS

It is to be understood the present invention is not limited to particular compositions or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The order of any method may be changed, and various elements may be added, reordered, combined, omitted, modified, etc.

It will be apparent to those skilled in the art that various modifications and variations can be made in the compositions, uses and preparations described herein without departing from the spirit or scope of the invention. Embodiments are more specifically explained by the following examples. It should be understood, however, that the present invention is not limited to these examples in any manner.

The following Comparative Example, Reference Example, Examples and Experimental Examples are intended to further illustrate several embodiments of extracts, compositions, and methods for the inhibition or prevention and treatment of arthritic disease.

Comparative Example 1. Preparation of Flower Bud Extract of *Lonicera japonica* THUNB 100 g of flower bud of *Lonicera japonica* THUNB purchased from Kyunghee Medical Center in Korea, was dried, cut into small pieces and added to 0.7 L of 50% ethanol. The solution was refluxed for 4 hours with stirring at 85° C. and the residue was filtered. The filtrate was concentrated and dried to obtain 35 g of the flower bud extract of *Lonicera japonica* THUNB to use as a comparative test sample (designated as 'LJ extract' hereinafter).

As shown in FIG. 1, it has been confirmed that the LJ extract contains 2.2% chlorogenic acid (w/w %) through chromatogram analysis (See, FIG. 1).

Comparative Example 2. Preparation of the Extract of *Anemarrhena asphodeloides* BUNGE 100 g of *Anemarrhena asphodeloides* BUNGE purchased from Kyunghee Medical Center in Korea, was air-dried, cut into small pieces and added to 0.7 L of 50% ethanol. The solution was refluxed for 4 hours with stirring at 85° C. and the residue was filtered. The filtrate was concentrated and dried to obtain 50 g of the extract of *Anemarrhena asphodeloides* BUNGE to use as a comparative test sample (designated as 'AA extract' hereinafter).

As shown in FIG. 2, it has been confirmed that the AA extract contains 2.3% mangiferin (w/w %) through chromatogram analysis (See, FIG. 1).

Example 1. Preparation of Mixed Herbal (KM-1) Extract 50 g of flower bud of *Lonicera japonica* THUNB and 50 g of *Anemarrhena asphodeloides* BUNGE purchased from Kyunghee Medical Center in Korea, were dried, mixed together, cut into small pieces and added to 0.7 L of 50% ethanol. The solution was refluxed for 4 hours with stirring at 85° C. and the residue was filtered. The filtrate was concentrated to the extent that the volume of solution reached to 0.1 L and the equal volume of butanol was added thereto to perform fractionation. Through repeated fractionation, the butanol soluble fraction was collected, concentrated and dried to obtain 9 g of the extract of mixed herbs, which was used as a test sample (designated as 'KM-1' hereinafter).

As shown in chromatogram analysis, it has been confirmed that the KM-1 extract contains 3% chlorogenic acid (w/w %) and 3.5% mangiferin (w/w %) through chromatogram analysis.

Example 2. Preparation of Mixed Herbal (KM-2) Extract 50 g of flower bud of *Lonicera japonica* THUNB and 50 g of *Anemarrhena asphodeloides* BUNGE purchased from Kyunghee Medical Center in Korea, were dried, mixed together, cut into small pieces and added to 0.7 L of 50% ethanol. The solution was refluxed for 4 hours with stiffing at 85° C. and the residue was filtered. The filtrate was concentrated and dried to obtain 40 g of the extract of mixed herbs, which was used as a test sample (designated as 'KM-2' hereinafter).

As shown in chromatogram analysis, it has been confirmed that the KM-2 extract contains 1.5% chlorogenic acid (w/w %) and 1.8% mangiferin (w/w %) through chromatogram analysis.

Example 3. Preparation of Mixed Herbal (KM-3) Extract 100 g of flower bud of *Lonicera japonica* THUNB and 50 g of *Anemarrhena asphodeloides* BUNGE purchased from Kyunghee Medical Center in Korea, were dried, mixed together, cut into small pieces and added to 0.7 L of 50% ethanol. The solution was refluxed for 4 hours with stirring at 85° C. and the residue was filtered. The filtrate was concentrated to the extent that the volume of solution reached to 0.1 L and the equal volume of butanol was added thereto to perform fractionation. Through repeated fractionation, the butanol soluble fraction was collected, concentrated and dried to obtain 11 g of the extract of mixed herbs, which was used as a test sample (designated as 'KM-3' hereinafter).

As shown in FIGS. 3 & 4, it has been confirmed that the KM-3 extract contains 4.5% chlorogenic acid (w/w %) and 2.1% mangiferin (w/w %) through chromatogram analysis (See, FIGS. 3 & 4).

Example 4. Preparation of Mixed Herbal (KM-4) Extract 100 g of flower bud of *Lonicera japonica* THUNB and 50 g of *Anemarrhena asphodeloides* BUNGE purchased from Kyunghee Medical Center in Korea, were dried, mixed together, cut into small pieces and added to 0.7 L of 50% ethanol. The solution was refluxed for 4 hours with stiffing at 85° C. and the residue was filtered. The filtrate was concentrated and dried to obtain 56 g of the extract of mixed herbs, which was used as a test sample (designated as 'KM-4' hereinafter).

As shown in chromatogram analysis, it has been confirmed that the KM-4 extract contains 2.2% chlorogenic acid (w/w %) and 1.4% mangiferin (w/w %) through chromatogram analysis.

Reference Example 1. Macrophage Cell Culture

Mouse macrophage cell line (Raw264.7, purchased from ATCC) was cultured in RPMI-1640 media (10% FBS, 2 mM 1-glutamine, 100 units/ml penicillin sodium, 100 units/ml streptomycin sulphate and 250 ng/ml amphotericin B). The culture cell was seeded on 24-well plate ($10^6$ cell/well) and treated with KM-1 (10, 50, 100, 200 µg/ml), KM-3 (10, 20, 40 µg/ml), positive control groups, i.e., Celecoxib (CEL, 100 µg/ml) and ETCP (SK Chemicals) (100, 200, 400 µg/ml) for 30 minutes. 1 µg/ml of LPS and 1 ng/ml of IFN- were added thereto, cultured in $CO_2$ incubator for 24 hours, and centrifuged for 5 minutes at 2000 rpm to collect the supernatant, which was used as a sample of following test.

Reference Example 2. Collagen-Induced Rheumatic Arthritis (CIA) Model

DBA/1 J mice were purchased from Chungang Experimental Animals (www.labanimals.co.kr, Korea). Equal volume of CFA (Complete Freund s Ajuvant) was added by drops to 2 ml of collagen solution (2 mg/ml) and mixed together well. 100 µl of the mixture was subcutaneously injected at 2.5 cm upper region from the tail fundus. 3 weeks after the injection, 2 ml of collagen solution mixed with the equal volume of WA (Incomplete Freund's Ajuvant) was injected at 1 cm upper region from the tail fundus at the dose of 100 µl. For 3 weeks, KM-1 (200 mg/kg), KM-3 (200 mg/kg) and Celecoxib (100 mg/kg) dissolved in CMC solution, were orally administrated thereto. CMC (Carboxymethylcellulose, Sigma) solution was administrated thereto as a negative control group.

Reference Example 3. Preparation of Cartilage Tissue

The joint cartilage of human was provided from the patient who had taken artificial joint surgery (Orthopedics Surgery Dep. of Kyunghee Medical Center). After revealing the surface of joint by surgery with a sterilized condition, about 200-220 mg of the articular surface tissue prepared from the articular cartilage of human and rabbit was dipped into DMEM medium (FBS, GIBCO BRL, USA) supplemented with 5% fetal bovine serum and 100 unit/ml of penicillin-streptomycin. The tissue was washed with the medium several times and then the articular tissue was cultured at 37° C. in humidified 95% $CO_2$ incubator. 1 or 2 days after the incubation, the medium was replaced with new basic medium containing inactivated 5% fetal bovine serum with heat treatment, 10 mM HEPES, and 100 unit/ml of penicillin-streptomycin, and 30 mg of the chondrocyte was transferred to 48-well plate.

After culturing for 1 hour, 5 ng/µl of interleukin-1α (IL-1α, R&D system, USA) was added to the medium to induce inflammation and various concentrations of test sample (KM-1), ETCP (SK Chemicals), Celecoxib (CEL, Pfizer Co., USA), and Glucosamine (GLUCO, Sigma Co., USA), i.e., 0.1, 0.2, and 0.4 mg/ml, were added thereto respectively. The medium was further cultured at 37° C. for 7 days, and the supernatant was collected, which had been stored at −20° C. to use as comparative test samples and test samples.

Reference Example 4. Reverse Transcription Polymerase Chain Reaction (RT-PCR)

The chondrocytic cell incubated according to the method disclosed in Reference Example 1, was treated with TRIzol reagent (Invitrogen Corporation, CA, USA) to isolate RNA and reverse transcription for 1 µg of total RNA was performed by adding buffer solution containing oligo$(dT)_{12}$ primer, Dntp (10 mM), 0.1 M dithiothreitol (DDT), reverse transcriptase and RNase inhibitor to the medium. The medium was incubated 42° C. for 60 minutes. PCR (polymerase Chain Reaction) using by the primers disclosed in Table 1 and Sequence (SEQ) I.D. 1 to 16, was performed by using 1 μg of each cDNA prepared from the above method, 2.5 unit of Taq polymerase enzyme (TaKaRa Taq™ Takara, Japan), 1.5 mM dNTP, 1×buffer solution (10 mM Tris-HCl pH 8.3, 50 mM KCl, Triton X-100), and 20 pM of each paired primers in Table 1 and Sequence I. D. 1 to 16. The solution was adjusted with distilled water to be total volume of 10 μl and then PCR was performed using by thermal cycler apparatus (Bio-Rad, USA) as follows: after denaturing at 94° C. for 5 minutes, the PCR is performed in the order of the reaction for 60 sec at 94° C., 60 sec at 55° C., and 90 sec at 72° C. The cycles were repeated 30 times and the last extension was performed at 72° C. for 5 minutes. The product produced by PCR was subjected to electrophoresis (5 V/cm) on 1.8% agarose gel and stained for 5 minutes with 2 μg/ml of ethidium bromide (EtBr). The stained product was washed for 10 minutes with distilled water and the result was determined at UV wavelength (260 nm).

were subjected to explant culture and subcultured for 2 times to use. Cartilage cell was isolated with type II collagenase, and subcultured twice in culture media condition to use. The chondrocyte was made into beads with alginate and seeded on the upper chamber, while the subchondral bone tissue cell was seeded on the lower chamber and cultured for 24 hours. 50 μg/ml of KM-3 was treated thereto for 14 days and the media was collected at every 7 days.

Experimental Example 1. Formalin Analgesia Test

In order to determine the analgesic activity of the extract prepared in Examples, formalin-induced analgesia test was performed according to the method disclosed in the literature as follows (Frazli-Tabaei S et al., *Behav. Pharmacol.*, 16, pp 613-619, 2005).

Male ICR mouse (Orient Bio, Japan) weighing from 20 to 25 g was acclimated for several days and each group consists of 8 mice. The test samples were administrated orally into the mice and 10% formalin solution (v/v, Sigma Co. USA)

TABLE 1

| Gene | | Primer Sequence |
|---|---|---|
| Col II | Sense | AAC ACT GCC AAC GTC CAG AT (SEQ. I.D. 1) |
| | Anti-sense | CTG CAG CAC GGT ATA GGT GA (SEQ. I.D. 2) |
| PG | Sense | GAG GTC GTG GTG AAA GGT GT (SEQ. I.D. 3) |
| | Anti-sense | GTG TGG ATG GGG TAC CTG AC (SEQ. I.D. 4) |
| MMP-1 | Sense | AAA GGG AAT AAG TAC TGG G (SEQ. I.D. 5) |
| | Anti-sense | GTT TTT CCA GTG TTT TCC TCA G (SEQ. I.D. 6) |
| MMP-3 | Sense | TGC GTG GCA GTT TGC TCA GCC (SEQ. I.D. 7) |
| | Anti-sense | GAA TGT GAG TGG AGT CAC CTC (SEQ. I.D. 8) |
| MMP-13 | Sense | GAT AAA GAC TAT CCG AGA C (SEQ. I.D. 9) |
| | Anti-sense | CGA ACA ATA CGG TTA CTC (SEQ. I.D. 10) |
| OCN | Sense | CAT GAG AGC CCT CAC A (SEQ. I.D. 11) |
| | Anti-sense | AGA GCG ACA CCC TAG AC (SEQ. I.D. 12) |
| Col I | Sense | TGA CCT CAA GAT GTG CCA CT (SEQ. I.D. 13) |
| | Anti-sense | GGG AGT TTC CAT GAA GCC AC (SEQ. I.D. 14) |
| GAPDH | Sense | GCT CTC CAG AAC ATC ATC CCT GCC (SEQ. I.D. 15) |
| | Anti-sense | CGT TGT CAT ACC AGG AAA TGA GCT (SEQ. I.D. 16) |

Reference Example 5. Collagenase-Induced Osteoarthritis (CIA) Model

Rabbits (Newzealand White Rabbit, Samtako, Korea) was acclimated with the environment for 1 week and 1.25 ml of collagenase (4 mg/ml, Sigma Co. USA) was injected into the synovial cavity of the rabbit's right knee. The weight of rabbit was measured before sample treatment and repeated for the interval of every week. Clinical symptoms such as walking behavior, the range of mobility, edema etc, were observed during the test. Each group (n=8) was treated with samples for four weeks, and the blood was sampled. The right knee was cut to be fixed with 10% formalin solution.

Reference Example 6. Co-Culture Model of Cartilage Cell and Subchondral Bone Tissue Cell The subchondral bone tissue and joint cartilage sample of human were provided from the patient taken artificial joint surgery (Orthopedics Surgery Dep. of Kyunghee Medical Center). The subchondral bone was crushed to pieces, and treated with type II collagenase for 30 minutes. The pieces was subcutaneously administrated to the left posterior limb one hour after the administration. The licking frequency of the foot sole was observed at the $1^{st}$ phase (from initial time to 5 minutes after the administration) and $2^{nd}$ phase (from 15 minutes to 20 minutes after the administration) to record. The inhibition rate (%) was calculated by setting the inhibition rate in positive control group treated with Celecoxib, a conventionally used NSAID, to 100.

TABLE 2

| | Concentration | Inhibition rate (%)* | |
|---|---|---|---|
| Group | (mg/kg) | $1^{st}$ phase | $2^{nd}$ phase |
| LJ(Comparative Example 1) | 400 | 110 | 70.0 |
| AA(Comparative Example 2) | 400 | 88.2 | 73.9 |
| KM-1(Example 1) | 400 | 121.8 | 123.8 |
| KM-2(Example 2) | 400 | 110.2 | 125.1 |
| KM-3(Example 3) | 400 | 141.7* | 165.8** |
| KM-4(Example 4) | 400 | 122.5 | 127.6 |

*Relative inhibition rate by setting the inhibition rate in positive control group treated with Celecoxib to 100

As shown in Table 2, it has been confirmed that the groups treated with KM-1, KM-2, KM-3 and KM-4 showed more potent analgesic effect than those treated with LJ and AA containing single herb, respectively, as well as the positive control group treated with Celecoxib. Especially, the analgesic effect of KM-3 showed most potent analgesic effect among them.

Experimental Example 2. MIA (Monosodium Iodoacetate) Model

In order to confirm the analgesic activity of the extract prepared in Examples, MIA (monosodium iodoactetate)-induced arthritis animal model test was performed with the procedure described in the literature (James D. Pomonis et al., Pain, 114, pp 339-346, 2005). Male SD rat (Orientbio. Japan) weighing from 200 to 220 g, was acclimated for several days and MIA (Sigma, cat# I2512, USA) dissolved in PBS was injected into the glenoid cavity of left hind knee to induce arthritis. After a week of recovery, the subjects induced with arthritis were selected by using incapacitance tester apparatus (Linton, Stoelting Co., Wood Dale, Ill.) and the subjects were grouped to consist of 8 animals for each group. On the $8^{th}$ day after the induction, the test samples were orally administered at the routine time for every day and the measurement of resulting data was started at one week after the administration for 3 weeks, once a week. The data was measured using by incapacitance tester (Linton, Stoelting Co., Wood Dale, Ill.) and calculated according to following Formula 1. The inhibition rate (%) was calculated by setting the inhibition rate in positive control group treated with Celecoxib, a conventionally used NSAID, to 100.

% Weight of left hind=({Weight of left hind/(Weight of left hind+Weight of right hind)}×100)    Formula 1

TABLE 3

| Group | Concentration (mg/kg) | Inhibition rate (%)* (at $3^{rd}$ week) |
| --- | --- | --- |
| LJ(Comparative Example 1) | 400 | 72.0 |
| AA(Comparative Example 2) | 400 | 89.1 |
| KM-1(Example 1) | 400 | 99.8 |
| KM-2(Example 2) | 400 | 94.5 |
| KM-3(Example 3) | 400 | 122.5 |
| KM-4(Example 4) | 400 | 112.8 |

*Relative inhibition rate by setting the inhibition rate in positive control group treated with Celecoxib to 100

As shown in Table 3, it has been confirmed that KM-1, KM-2, KM-3 and KM-4 showed more potent analgesic effect than LJ and AA treated with single herbs, respectively. Especially, the pain inhibition effect of KM-3 and KM-4 was superior to that of KM-1 and KM-2, respectively, as well as the positive control Celecoxib. Especially the analgesic effect of KM-3 was able to significantly inhibit the pain the most.

Experimental Example 3. Radiation-Induced Tail Flick Analgesia Test

In order to confirm the analgesic effect of the extract prepared in Examples, radiation-induced tail flick analgesia test was performed with the procedure described in the literature (Shaw F Z et al., Brain Res., 911(2), pp 105-115, 2001).

Male ICR mouse (Orientbio. Japan) weighing from 20 to 25 g was acclimated for several days and grouped to 8 animals for each group. Test samples were orally administrated thereto. One hour after the treatment, the medianus of tails was irradiated with infrared ray to determine the time until the avoidance response appeared. The inhibition rate (%) was calculated by setting the inhibition rate in positive control group treated with Celecoxib, a conventionally used NSAID, to 100.

TABLE 4

| Group | Concentration (mg/kg) | Inhibition rate (%)* |
| --- | --- | --- |
| LJ(Comparative Example 1) | 400 | 95.9 |
| AA(Comparative Example 2) | 400 | 120.6 |
| KM-1(Example 1) | 400 | 145.7 |
| KM-2(Example 2) | 400 | 128.5 |
| KM-3(Example 3) | 400 | 149.1 |
| KM-4(Example 4) | 400 | 131.8 |

*Relative inhibition rate by setting the inhibition rate in positive control group treated with Celecoxib to 100

As shown in Table 4, it has been confirmed that KM-1, KM-2, KM-3 and KM-4 showed more potent analgesic effect than LJ and AA treated with single herbs, respectively. Especially, the pain inhibitory effect of KM-3 and KM-4 was superior to those of KM-1 and KM-2, respectively, as well as the positive control Celecoxib. Especially, the group treated with KM-3 showed most potent inhibiting effect among them.

Experimental Example 4. Paw Pressure Analgesia Test

In order to confirm the analgesic effect of the extract prepared in Examples, rat paw pressure analgesia test was performed with the procedure described in the literature (Randall L O and Selitto J J, Arch Int. Pharmacodyn., 111, pp 409-419, 1957).

Male SD rat (Orientbio. Japan) weighing from 180 to 200 g was acclimated for several days and grouped to 8 animals for each group. Test samples were orally administrated thereto. One hour after the treatment, 2% carrageenan (Sigma Co., USA) was subcutaneously injected into the sinistral ramus posterior of the rat. 3 hours after the injection, the weight at the time that avoidance response appeared, was measured by using analgesic meter (Ugobasile, Italy). The inhibition rate (%) was calculated by setting the inhibition rate in positive control group treated with Celecoxib, a conventionally used NSAID, to 100.

TABLE 5

| Group | Concentration (mg/kg) | Inhibition rate (%)* |
| --- | --- | --- |
| LJ(Comparative Example 1) | 400 | 82.5 |
| AA(Comparative Example 2) | 400 | 109.5 |
| KM-1(Example 1) | 400 | 130.4 |
| KM-2(Example 2) | 400 | 115.0 |
| KM-3(Example 3) | 400 | 147.8 |
| KM-4(Example 4) | 400 | 131.2 |

*Relative inhibition rate by setting the inhibition rate in positive control group treated with Celecoxib to 100

As shown in Table 5, it has been confirmed that KM-1, KM-2, KM-3 and KM-4 showed more potent analgesic effect than LJ and AA treated with single herbs, respectively. Especially, the pain inhibitory effect of KM-3 and KM-4 was superior to those of KM-1 and KM-2, respectively, as well as the positive control Celecoxib. Especially, the group treated with KM-3 showed most potent inhibitory effect among them.

Experimental Example 5. Hot Plate Pain Test

Hot plate pain test was performed with the procedure described in the literature (Pharmacological report, 60 (2008) pp 409-414).

Male ICR mouse (Orientbio. Japan) weighing from 15 to 20 g was acclimated for several days and grouped to 8-9 animals for each group. Test samples were orally administrated thereto. One and two hour after the treatment, the mouse was put into plastic cylinder, of which temperature was maintained at 55±1° C. to determine the time when the mouse licked sole of the feet or jumped. The cut-off time was set to 15 seconds, and the inhibition rate (%) was calculated by setting the inhibition rate in positive control group treated with Celecoxib, a conventionally used NSAID, to 100.

TABLE 6

| Group | Concentration (mg/kg) | Inhibition rate (%) |
|---|---|---|
| LJ(Comparative Example 1) | 400 | 82.5 |
| AA(Comparative Example 2) | 400 | 109.5 |
| KM-3(Example 3) | 100 | 121.8 |
|  | 200 | 127.2 |
|  | 400 | 167.6 |

*Relative inhibition rate by setting the inhibition rate in positive control group treated with Celecoxib to 100

As shown in Table 6, it has been confirmed that KM-3 showed more potent analgesic effect than LJ and AA treated with single herbs, respectively. Especially, the pain inhibitory effect of KM-3 was superior to that of the positive control Celecoxib.

Experimental Example 7. Acetic-Acid Induced Writhing Test

Acetic-acid induced writhing test was performed to determine the anti-inflammatory effect with the procedure described in the literature (H. O. J collier et al., Br. J. Pharmac. Chemother., 32, pp 295-310, 1968).

Male ICR mouse (Orientbio. Japan) weighing from 20 to 23 g was acclimated for several days and grouped to 5-8 animals for each group. Test samples were orally administrated thereto, and one hour after the treatment, 1% acetic acid solution (Sigma, USA) was intraperitoneally administrated thereto. After the injection, the writhing number determined from 5 to 20 minutes was recorded. The inhibition rate (%) was calculated by setting the inhibition rate in positive control group treated with Celecoxib, a conventionally used NSAID, to 100.

TABLE 7

| Group | Concentration (mg/kg) | Inhibition rate (%) |
|---|---|---|
| LJ(Comparative Example 1) | 400 | 32.5 |
| AA(Comparative Example 2) | 400 | 39.5 |
| KM-3(Example 3) | 100 | 61.2 |
|  | 200 | 67.8 |
|  | 400 | 77.9 |

*Relative inhibition rate by setting the inhibition rate in positive control group treated with Celecoxib to 100

As shown in Table 7, it has been confirmed that KM-3 showed more potent analgesic effect than U and AA treated with single herbs, respectively. Especially, the pain inhibition effect of KM-3 was superior to that of the positive control Celecoxib.

Experimental Example 8. Croton Oil Induced Ear Edema Test

Croton oil induces various skin inflammations such as rash, swelling, blister and so on. In order to determine the anti-inflammatory activity of the extract, following test using croton oil-induced ear edema was performed according to method disclosed in the literature (Gabor M, Mouse ear inflammation models and their pharmacological applications, Published by Akademiai Kiado, Budapest, pp 24-28, 2000).

Male ICR mouse (Orientbio. Japan)) weighing from 20 to 25 g was used as an experimental animal and each group consists of 6 mice. The test samples were administrated orally and after 1 hour, 2.5% croton oil dissolved in acetone was spread on the inner and outer surface of right ear to induce ear-edema. After 4 hours, the increased rate of ear thickness was calculated by comparing with that of left ear of dead mouse with ether using by thickness gauge according to velocity transformation technique (Patrick et al., Toxicol. Appl. Pharmacol., 81, pp 476-490, 1985).

The inhibition rate (%) was calculated by setting the inhibition rate in positive control group treated with Celecoxib, a conventionally used NSAID, to 100.

TABLE 8

| Group | Concentration (mg/kg) | Inhibition rate (%)* |
|---|---|---|
| LJ(Comparative Example 1) | 400 | 100.9 |
| AA(Comparative Example 1) | 400 | 88.7 |
| KM-1(Example 1) | 400 | 114.7 |
| KM-2(Example 2) | 400 | 105.8 |
| KM-3(Example 3) | 400 | 143.9 |
| KM-4(Example 4) | 400 | 121.7 |

*Relative inhibition rate by setting the inhibition rate in positive control group treated with Celecoxib to 100

As shown in Table 8, it has been confirmed that KM-1, KM-2, KM-3 and KM-4 showed more potent analgesic effect than U and AA treated with single herbs, respectively. Especially, the pain inhibition effect of KM-3 and KM-4 was superior to those of KM-1 and KM-2, respectively, as well as the positive control Celecoxib. Especially, the group treated with KM-3 showed most potent anti-inflammatory effect among them.

Experimental Example 9. Carrageenan-Induced Rat Paw Edema Test

In order to determine the analgesic activity of the extract, carrageenan-induced rat-paw edema test was performed as follows.

Male Wister mouse (Orient Bio, Japan) weighing from 20 to 25 g was acclimated for several days and each group consists of 8 mice. The test samples were administrated orally into the mice in an amount of 100-400 mg/kg and carrageenan dissolved in a physiological solution was subcutaneously administrated to the left posterior limb to induce inflammation. The degree of the edema at the sole of left hind was compared with that of right hind with careful of contaminant using by a plethysmometer apparatus at regular intervals.

Celecoxib was orally administrated as a positive control group in an amount of 100 mg/kg (body weight). The inhibition rate (%) was calculated by setting the inhibition rate in positive control group treated with Celecoxib, a conventionally used NSAID, to 100.

TABLE 9

| Group | Concentration (mg/kg) | Inhibition rate (%)* |
|---|---|---|
| LJ(Comparative Example 1) | 400 | 90.9 |
| AA(Comparative Example 1) | 400 | 88.7 |
| KM-1(Example 1) | 400 | 94.7 |
| KM-2(Example 2) | 400 | 95.8 |
| KM-3(Example 3) | 400 | 126.9 |
| KM-4(Example 4) | 400 | 100.7 |

*Relative inhibition rate by setting the inhibition rate in positive control group treated with Celecoxib to 100

As shown in Table 9, the test group treated with KM-3 orally administrated in the amount of 400 mg/kg showed potent inhibitory effect on the edema, moreover, more effective than that treated with Celecoxib.

Experimental Example 10. Inhibition of No (Nitric Oxide) Production

In order to confirm the inhibitory effect of the extract on NO activity, following experiment was performed according to the method disclosed in the literature (International *Immunopharmacology*, 7(6), pp 871-8, 2007(June)).

Nitrite accumulation, an indicative of NO synthesis, was measured by applying Griess reaction. Peritoneal macrophage was incubated in RPMI (GIBCO BRL, USA) medium containing inactivated fetal bovine serum (FBS, GIBCO BRL, USA) with heat, 100 unit/ml of penicillin and 100 unit/ml of streptomycin sulfate, and incubated at 37° C. in 5% $CO_2$ incubator. 100 μg/ml of KM-1 and 50 mg/ml of Celecoxib (Pfizer Ltd., USA) were added to 96-well plates and 30 mins after the treatment, 1 μg/ml of LPS and 1 ng/ml of IFN-γ were treated thereto to incubate in 5% $CO_2$ incubator. After incubating for 96 hours, 100 μl of collected cell culture medium was mixed with 100 μl of 5% (v/v) Griess reagent containing 1% (w/v) sulfanilamide, 0.2% N-naphthylethylene diamine 2 HCl and 2.5% $H_3PO_4$, and the well plates were replaced with new 96-well plates. The absorbance was measured at 550 nm within 10 mins by using micro plate reader (Power Wave 340, Bio-Tek, USA). Fresh medium in all experiments was used as non-treatment group. The amount of NO in the medium was calculated based on the generated sodium nitrite ($NaNO_2$) standard curve and result was showed in FIG. 5.

As shown in FIG. 5, by comparing the amount of produced NO which stimulates the release of inflammatory cytokines resulting in the induction of inflammation with that in positive control group, it has been confirmed that KM-1 and KM-3 showed more potent inhibitory effect than positive control group.

Experimental Example 11. Determination of Inflammatory Mediators ($PGE_2$)

In order to determine the inhibitory effect of test samples on the release of $PGE_2$ (#SKGE 004, R&D systems, USA) in the supernatant of Reference Example 1, the test was performed according to the ELISA method disclosed in the literature (Dovedi S J, et al., *J. Urol.*, 174(1), pp 332-337, 2005).

The serum was diluted to 1:500 with phosphate buffer and 50 μl of the dilution was added to supernatant. The pre-coated plates with goat anti-mouse prostaglandin $E_2$ monoclonal IgG were treated with various concentrations of KM-1 (10, 50, 100, 200 μg/ml), KM-3 (10, 20, 40, 80 μg/ml), Celecoxib (CEL, 80 μg/ml) and ETCP (80 μg/ml), reacted with together, and the amount of synthesized $PGE_2$ was measured against the serial dilution of standard $PGE_2$ to quantify.

At the result, the groups treated with KM-1 and KM-3 showed potent inhibitory effect on the release of $PGE_2$, corresponding to Celecoxib treated group (See FIG. 6).

Experimental Example 12. Determination of Inflammatory Cytokine (IL-1β, IL-6)

In order to determine the inhibitory effect of test samples on releasing amount of IL-1β, IL-6 (#200-LA, R&D systems, USA) in the supernatant of Reference Example 1, the ELISA method was performed as follows.

To determine the anti-inflammatory effect of the groups treated with various concentrations of each KM-1 (10, 50, 100, 200 μg/ml), KM-3 (10, 20, 40, 80 μg/ml), Celecoxib (CEL, 100 μg/ml), ETCP (100, 200, 400 μg/ml) and Indo (30 μg/ml, indomethacin), 100 μl of the supernatants of each group was added to the pre-coated plate with each antibody, and reacted for 1 hour to develop. The optical density of the reacted solution was determined at 540 nm. As shown in FIG. 7-A, the group treated with KM-1 showed significantly inhibitory effect on the release of cytokine IL-1β in a dose dependent manner. Moreover, as shown in FIGS. 7-B and 7-C, the group treated with KM-3 showed corresponding inhibitory effect on the release of IL-1β and IL-6 expression to those with Celecoxib and ETCP.

Experimental Example 13. Collagen-Induced Arthritis

The anti-inflammation and immune inhibitory effect was determined using the animal model of Reference Example 2.

2 ml of collagen solution (2 mg/ml) was mixed with the equal volume of CFA (Complete Freund's Adjuvant) in a drop wise manner. 100 microliter of the mixture solution was subcutaneously injected to the region positioned at 2.5 cm above the tail fundus of DBA/1J mouse (Chungang Experimental animal, Korea). 3 weeks after the injection, 2 ml of collagen solution was mixed with the equal volume of IFA (Incomplete Freund's Adjuvant) and 100 microliter of the solution was subcutaneously injected the region positioned at 1 cm upper from the tail fundus again. Test samples were orally administrated thereto for 3 weeks. 3 weeks after the treatment, the degree of edema was measured and the concentration of COMP (Cartilage Oligomeric matrix protein, Animal COMP ELISA, AnaMar Medical Co., Sweden), a representative indicator for determining the degree of cartilage destruction, the number of total lymphocyte in spleen, and collagen-specific antibody (Anti-collagen antibody assay kit, Chondrex Co., USA), which has been known as the main indicator among anti-inflammation effectors since the antibody reproduced by dint of collagen injection, attacks the cartilage site. As shown in FIGS. 8 to 11, the test group treated with KM-1 and KM-3 showed potent anti-inflammatory activity corresponding to the positive control group treated with Celecoxib. Especially, the anti-inflammatory effect of KM-3 was superior to that of KM-1.

Experimental Example 14. Protective Effect on Cartilage-Effect on Dissociation of Glycosaminoglycan In order to determine the protective effect on the articular cartilage tissue of human, 1,9-dimethylmethylene blue (DMB) assay method was performed by the procedure disclosed in the literature to confirm the inhibitory effect on the degradation of GAG consisting of proteglycan (French M M et al., *Ann. Biomed. Eng.*, 32(1), pp 50-56, 2004).

The concentration of GAG in the culture medium of cartilage tissue incubated with the procedure disclosed in Reference Example 3 was measured by determining the amount of polyanionic substance produced by being reacted with blyscan dye solution and chondroitin sulfate was used as a standard. 50 µl of culture medium treated with the extract of KM-1 (0.1, 0.2, and 0.4 mg/ml), KM-3 (0.1, 0.2, 0.4 mg/ml), Celecoxib (CEL, Pfizer, USA) (20, 100 µg/ml), glucosamine (GLUCO, Sigma, USA)(100, 200, 400 µg/ml), mangiferin (100, 200, 400 µg/ml) and cholorogenic acid (100, 200, 400 µg/ml) as positive controls, respectively, was mixed with 500 µl of blyscan dye solution and reacted for 30 minutes at room temperature. The reactant was centrifuged at 12,000 rpm for 10 minutes and the precipitate was dissolved in blyscan dye dissociation solution. The amount of spectroscopic GAG was determined at 540 nm and the inhibition rate was expressed based on the amount of degraded GAG induced by interleukin-1α (IL-1α).

As shown in FIG. 12, the groups treated with KM-1, KM-3, and standard components, i.e., mangiferin and chlorogenic acid, potently inhibited the degradation of GAG to the medium, which confirms that the extract inhibited the degradation of proteoglycan in cartilage induced by IL-1α in a dose dependent manner, moreover, it inhibited the degradation of GAG in human cartilage tissue comparing with Celecoxib and glucosamine used as controls.

Experimental Example 15. Gene Expression of Proteoglycan Gene

The expression of proteoglycan and Col II gene collected from the cartilage tissue and chondrocytic cell of rabbit in above Reference Example 3 was determined and the test was performed by using reverse transcription polymerase chain reaction (RT-PCR) with the method disclosed in Reference Example 4.

KM-1 (10µ, 100, and 200 µg/ml), KM-3 (5, 10, 20 µg/ml), mangiferin (0.01, 0.1, 1 µg/ml) and cholorogenic acid (0.01, 0.1, 1 µg/ml) were used in the experiment.

As shown in FIG. 13, the extract potently increased the gene expression of proteoglycan and Col II gene in a dose dependent manner, of which expressions were inhibited by the treatment of IL-1α in cartilage tissue.

Experimental Example 16. Determination of the Concentrations of MMP-1 and MMP-13

Matrix metalloproteinase (MMP), a protease cleaving the protein in cartilage tissue, destroys the cartilage tissue in rheumatic arthritis and osteoarthritis resulting in exacerbating arthritis. Accordingly, the inhibition of the enzyme reproduction is main target to protect articular cartilage (Nagase H and Woessner J F Jr., *J. Biol. Chem.*, 274(31), pp 21491-21494, 1999).

The inhibitory effect on MMP reproduction using human cartilage tissue medium prepared in Reference Example 3 was determined by using ELISA kit (MMP-1 kit, MMP-13 kit, Biomol Research Lab., Inc., PA, USA), according to the manual of manufacture and thiopeptolide (Ac-Prop Leu-Gly-[2-mercapto-4-methyl-pentanoyl]-Leu-Gly-OC$_2$H$_5$) was used as a colorimetric substrate excised by MMP-1 (collagenase-1) and MMP-13 (collagenase-13). In order to measure proteolytic activity, each 25 µl of medium was added to 96-well plate with 50 µl of the substrate to incubate at 37° C. for 1 hr and the optical density was measured by ELISA reader (Molecular devices, USA) at 450 nm. The activity of each sample on MMP-1 and MMP-13 was determined by calculating the MMP (%) of medium in each well.

As shown in FIGS. 14 and 15, the groups treated with KM-1, KM-3 and the standard components, i.e., mangiferin and chlorogenic acid, significantly inhibited the activity of collagenase MMP-1 and MMP-13 in a dose dependent manner. The groups treated with KM-1 and KM-3 showed equivalently inhibitory effect with that of ETCP, used as positive controls and more potent inhibitory effect than those of Celecoxib and glucosamine treated group.

Experimental Example 17. Inhibition of the Gene Expression of MMP-1, MMP-3 and MMP-13

To determine the inhibitory effect of the extract on the reproduction of MMPs (Matrix Metalloproteinases) using the cartilage tissue and chondrocyte of rabbit prepared in Reference Example 3, RT-PCR was performed according to the procedure disclosed in Reference Example 4.

As shown in FIG. 16, the extract significantly inhibited the gene expression of MMP-1, MMP-3 and MMP-13 in cartilage cell in a dose dependent manner.

Experimental Example 18. Cell Toxicity Test

In order to examine the effect of the extract on the viability of chondrocyte, the cell toxicity test using the cartilage tissue and chondrocyte of rabbit prepared in Reference Example 3 was performed according to the method disclosed in the literature (Cakmak O et al., *Arch Facial Plast. Surg.*, 7(6), pp 406-409, 2005).

As an indicative of chondrocyte viability, the activity of cytoplasmic enzyme lactate dehydrogenase (LDH) was measured by conventionally available kit (LDH kit, Promega Corp., Madison, Wis., USA) assay was performed according to the procedure disclosed in the literature (Hussain S M et al., *Toxicol. In Vitro*, 19(7), pp 975-983, 2005).

To determine the activity of LDH, the negative control group and test groups treated with KM-1 (0.1, 0.2, and 0.4 mg/ml), KM-3 (0.1, 0.2, and 0.4 mg/ml) and positive control group (ETCP, CEL, GLUCO) was incubated to collect the culture medium. After dissolving the substrate mixed powder (diaphorase, lactate, NAD) in TBT solution (Tris-buffered Tetrazolium, #G1781, Promega), 50 µl of medium was mixed with 50 µl of substrate mixture to react together at room temperature for 30 minutes. After adding 50 µl of stopping solution thereto, the absorbance of culture medium was measured at 490 nm to determine the activity of LDH. As shown in FIG. 17, the groups treated with KM-1 and KM-3 did not affect on the viability of cultured human cartilage tissue for 7 days. Accordingly, it has been confirmed that the extract did not show cell toxicity in cartilage tissue, which confirmed that it is safe.

Experimental Example 19. Cartilage Protection Signal Transduction Phosphorylation Procedures To determine whether the extract is involved in the signal pathway among MAPK (pERK, pp 38, pJNK) in connection with the cartilage protection mechanism and involved in the inhibition of the differentiation of cartilage cell and joint regeneration to activate cartilage cell, following experiment was performed using the protein obtained from Reference Example 3 according to the procedure as follows.

The protein was added to lysis buffer to mixed together, reacted for 1 hour at 4° C., and centrifuged at 15,000×g to obtain the supernatant. The supernatant was kept in refrigerator; a part of them was used to determine the amount of protein using by BCA solution. 20 µg of protein was performed to electrophoresis on 12% acrylamide gel, transferred to nitrocellulose paper and blocked for 1 hour with 5% skim milk. The antibodies against to pERK, pp 38, pJNK were treated thereto for 2 hours, and washed with TBST solution. Each secondary antibody against those was reacted for 1 hour, washed and exposed by ECL solution kit to develop.

As shown in FIG. 18, the groups treated with KM-3 and the standard components, i.e., mangiferin and chlorogenic acid, inhibited the activity of pERK, and the activities of pJNK and pp 38 resulting in cell death signal transduction were potently inhibited, which denotes cartilage protecting effect.

Experimental Example 20. Observation on Eye (CIA Animal Model)

In order to confirm the effect on the recovery of osteoarthritis, following experiment was performed using by the CIA model rabbits prepared in Reference Example 5 as follows.

0.5% carboxymethyl cellulose (CMC) for negative control (vehicle), KM-1 (100, 200, 400 mg/kg), KM-3 (100, 200, 400 mg/kg), Celecoxib (CEL, 100, 200 mg/kg), glucosamine (400 mg/kg) for treatment group were orally administrated to the rabbits at the dose of 200 ml/day. The degree of edema and motility range of the CIA rabbit was quantitatively determined at the interval of one week for 4 weeks by dividing into 4 scores and the mean values of the data was calculated.

As shown in FIG. 19, KM-1 and KM-3 significantly inhibited the edema of osteoarthritis and further enhanced motility range of the rabbit.

Experimental Example 21. Recovery of Cartilage Tissue Determined by Histochemical Staining (CIA Animal Model)

In order to confirm the effect on the recovery of cartilage tissue or chondrocyte, following histochemical staining method using CIA model rabbits was performed according to the method disclosed in the literature (Byron C R et al., Am. J. Vet. Res., 66(10), pp 1757-1763).

The cultured slices of the cartilage tissue of rabbit prepared in Reference Example 5 was fixed in 10% neutral formalin, subjected to decalcification, and embedded with paraffin.

The paraffin block was sectionalized to the thickness of 5 µm and attached to poly-L-lysine-coated glass slide (Sigma, USA). The slices were subjected to de-paraffinization, hydration process and staining with hematoxylin and eosin.

In order to stain each proteoglycan and collagen in cartilage tissue, the slices was stained with safranin O (Sigma, USA) and trichrome (Sigma, USA)(Muir H M et al., Histology, Churchill Livingstone, Edinburgh, pp 177-198, 1986).

The pathologist who had not recognized the information on the sample was interpreted the stained slides and the slide was photographed with the lens (200×).

As shown in FIG. 20, although the cartilage thickness of rabbit Femur chondyle in control group has been thinned, the cartilage of femur chondyle of the group treated with KM-1 and KM-3 has been recovered to the similar level to that in normal group. Especially, KM-3 treated group showed more potent recovering effect on cartilage thickness than KM-1 treated group. The results were transformed to be scored and graded according to the method disclosed in the literature (Kikuchi et al., *Osteoarthritis,* 4, pp 99-110, 1996).

As shown in Table 10, the total score summed up with various factors, i.e., the injury of cartilage surface, the destruction and cleavage of cartilage, distribution of cartilage cell and etc., in the test group treated with KM-1 showed more decreased value, to about 2.2 lower level comparing with that in the control group treated with 0.5% CMC, which confirmed that the extract showed potent recovery effect on the cartilage tissue.

TABLE 10

|  | 0.5 % CMC treated group | KM-1 treated group | KM-3 treated group |
| --- | --- | --- | --- |
| | Femur condyle | | |
| Injury of cartilage surface | 3.7 ± 1.2 | 1.9 ± 0.5 | 1.2 ± 0.3 |
| Cartilage destruction | 3.1 ± 0.9 | 1.6 ± 0.5 | 1.3 ± 0.4 |
| Tearing/Cutting | 3.3 ± 0.7 | 1.3 ± 0.3* | 1.3 ± 0.2* |
| Disorganization of cartilage cell | 3.9 ± 0.6 | 1.8 ± 0.6 | 1.4 ± 0.4* |
| Loss of cartilage cell | 2.8 ± 0.8 | 1.1 ± 0.2* | 1.1 ± 0.2* |
| Lump formation | 2.6 ± 0.8 | 1.0 ± 0.3* | 0.9 ± 0.1* |
| Total score | 19.4 ± 5.0 | 8.7 ± 2.4 | 7.2 ± 1.6* |

Each data represents the mean ± S.D. (n = 5)
*$P < 0.01$ compared to 0.5% CMC treated group.

Experimental Example 22. Cartilage Protecting Effect (CIA Animal Model)

In order to confirm the protecting effect from the erosion of cartilage tissue or chondrocyte, Masson-Trichrome dye for staining collagen and the safranin dye for proteoglycan in the joint paraffin tissue of CIA animal model obtained from Reference Example 5 using CIA model rabbits was performed as follows.

The paraffin was removed from the slide tissue, and the slide tissue went through saline soaking. The tissue was stained with Weigert's iron hematoxylin solution for 10 minutes, i.e., Safranin O staining method, and soaked in running water for 10 minutes. Thereafter, the tissue was further stained with fast green (FCF) solution for 5 minutes and rinsed for 10-15 seconds with 1% acetic acid. The slide was stained with 0.1% safranin O for 5 minutes again, dehydrated and sealed. Each stained slide was observed by microscopy and the intensity of the dye content was transformed into countable values using by I-solution™ program (IMTechnology, England). As shown in FIG. 21 and FIG. 22, the cartilage thickness of rabbit Femur chondyle of CIA animal model has been thinned, whereas the cartilage of femur chondyle of the group treated with KM-3 has been recovered to the similar level to that in normal group. Especially, KM-3 treated group showed more potent recovering effect on cartilage thickness than other treatment groups.

Experimental Example 23. Cartilage Recovery Effect (CIA Animal Model)

In order to confirm the protecting effect from the erosion of cartilage tissue or chondrocyte, an immunohistochemistry test using by the antibody (anti-CD105, anti-CD73) recognizing the antigen of mesenchymal stem cell and proteoglycan antibody (anti-aggrecan), in CIA animal model obtained from Reference Example 5 was performed as follows.

The paraffin was removed from the tissue attached slide and the slide was washed. The tissue was reacted with 3% hydrogen peroxide for 5 minutes, washed with TBS, treated with proteinase K for 20 minutes, and washed again. The tissue was reacted with goat serum for 30 minutes, and then with antibodies such as CD105, CD73 antibody etc to wash with TBS. After reacting with secondary antibody against to peroxidase-conjugated goat anti-mouse IgG, the tissue was reacted with streptavin-labeled antibody, stained with DAB, and mounted after contrast-staining with hematoxylin to observe by microscope.

As shown in FIG. 23, in the case of the subchondral bone of CIA animal model, there showed little expression amount of mesenchymal stem cell-surface antigen and proteoglycan antigen, while there showed abundantly increased in the group treated with KM-3. In particular, the group treated with KM-3 recovers the damaged subchondral bone due to the increased proteoglycan, a component of cartilage.

Experimental Example 24. Cartilage Recovery Effect (Co-Culture of Cartilage Cell and the Tissue Cell of Subchondral Bone)

In order to confirm the recovering effect from the erosion of cartilage tissue, the cytokine and differentiation marker of bone, and the amount of GAG degradation were performed as follows.

The culture media obtained from Reference Example 6 was used to determine the ALP activity. The cell was performed to lysis, collected to determine the intracellular alkaline phosphatase, which degrades p-nitrophenylphosphate (Sigma-Aldrich, USA) into p-nitrophenol and phosphate by measuring their optical density at 405 nm. Also, the level of IL-1β(#200-LA, R&D system, USA), VEGF (#DM900, R&D system, USA) and MMP-13 (#DM1300, R&D system, USA) in the media were determined by adding 100 μl of the supernatant of each group to the pre-coated plate with each antibody to react with together for 1 hour, and measuring the optical density at 540 nm. The concentration of GAG was determined by measuring the amount of the produced polyanionic substances resulting from the reaction with Blyscan dye solution, and chondroitin sulfate was used as a standard substance.

TABLE 11

|  | Control(7 d) | KM-3 (7 d, 50 μg/ml) |
|---|---|---|
| | ALP (nmol/μg DNA) | |
| NSC | 2.1 ± 0.1 | 2.2 ± 0.7 |
| SC | 3.8 ± 0.3 | 3.1 ± 0.4 |
| | IL-1beta (pg/μg DNA) | |
| NSC | 1.4 ± 0.3 | 1.7 ± 0.4 |
| SC | 1.5 ± 0.2 | 1.2 ± 0.5 |
| | VEGF (pg/μg DNA) | |
| NSC | 148.9 ± 12.1 | 144.5 ± 12.9 |
| SC | 752.9 ± 23.7### | 139.1 ± 17.6*** |
| | TGF-beta1 (pg/μg DNA) | |
| NSC | 221.1 ± 10.9 | 244.5 ± 22.8 |
| SC | 421.1 ± 21.1### | 219.8 ± 17.9** |
| | MMP-13 (pg/μg DNA) | |
| NSC | 137 ± 20.7 | 123 ± 11.8* |
| SC | 1776 ± 44.5### | 326 ± 21.3*** |

*$p < 0.05$,
**$p < 0.01$,
***$p < 0.001$ compared with control group,
$p < 0.001$ compared with NSC.

As shown in Table 11, in the case that the subchondral bone tissue cell was only cultured, the extract KM-3 did not affect on the level of cytokine, growth hormone and collagenase whereas in the normal subchondral bone tissue cell, there showed significantly inhibition from those of growth hormone and collagenase in the abnormal tissue cell.

Also, as shown in FIG. 24, the GAG degradation was significantly inhibited where the subchondral bone tissue cell and cartilage cell were co-cultured.

Experimental Example 25. Single Oral Dose Toxicity Test

In order to confirm the safety of the extract, following single oral dose toxicity test using by female Sprague-Dawley rat (Coretech, co, Korea) was performed according to the Up & Down method disclosed in the literature or implement (OECD (2006): OECD Guidelines for the testing of chemicals No. 425: Acute oral toxicity: Up-and-Down-Procedure (UPD)).

The KM-3 extract was orally administrated to each group consisting of 3 rats once at the dose of 5000 mg/20 ml/kg and the symptoms of rats were observed for 14 days. After administrating the extract, all the clinical changes i.e., mortality, clinical signs, and body weight changes was observed At the result, there did not show any changes in mortality, clinical signs, body weight changes and gross findings in any group or either gender. Furthermore, there showed any toxicity in test group treated with 5000 mg/kg of the extract.

Accordingly, it has been confirmed that the extract was potent and safe substance of which MLD (Minimum Lethal Dose) is presumed to over 5000 mg/kg.

Experimental Example 26. Two Week's Repetitive Oral Dose DRF Toxicity Test

In order to confirm the safety of extract, following two week's repetitive oral dose DRF toxicity test using by female Sprague-Dawley rat (Coretech, Co, Korea) was performed according to the method disclosed in the literature (Greaves, P. (2000): Histopathology of preclinical toxicity studies: Interpretation and relevance in drug evaluation, Elsevier).

The KM-3 extract was orally administrated to three groups of SD rats, i.e., the test groups treated with 1000 mg/kg/day of KM-3 and that 2000 mg/kg/day of KM-3, and the control group treated with only adjuvant (0.5% CMC-Na; Sodium Carboxy methyl Cellulose) consisting of 5 rats and the symptoms of rats were observed for 14 days. After administrating the extract, all the clinical changes i.e., mortality, clinical signs, and body weight changes was observed After administrating the extract, all the clinical changes i.e., mortality, clinical signs, body weight changes was observed and blood test such as haematological test and hematological biochemistry test was performed. The abnormal changes of abdominal organ and thoracic organ were observed after autopsy. There did not show any changes in mortality, clinical signs, body weight changes and gross findings in any group or either gender. Furthermore, there showed any toxicity in test group treated with 1000 mg/kg/day of KM-3 and 2000 mg/kg/day of KM-3. Accordingly, it has been confirmed that the extract was potent and safe substance showing NOEL (less than 1000 mg/kg) and NPAEL (2000 mg/kg) in oral administration.

Experimental Example 27. Bacterial Reverse Mutation Test

To evaluate the genetic toxicity in bacteria, bacterial reverse mutation test using by histidine-required strains of *Salmonella typhimurium*, i.e., 5 strains TA100, TA1535, TA98, *Escherichia coli* WP2 uvrA and TA1537 (Molecular toxicology Inc. P.O. Box 1189 Boone, N.C. 28607, USA) and tryptophan required strain of *Escherichia coli*, i.e., WP2 uvrA were performed according to the method disclosed in the literature (Maron D. M. and Ames B. N. (1983): Revised methods for the *Salmonella* mutagenecity test. Mutat. 113: 173-215).

50 mg/ml of KM-3 prepared in Example 2 was dissolved in DMSO and treated to the bacteria. The range was set to 62, 185, 556, 1667, and 5000 g/plate against each strain where the metabolic activation system was applied and non-applied, respectively, and negative control (DMSO; Sigma-Aldrich Company) and positive controls (2-aminoanthracene, Sodium azide, 4-nitroquinoline N-oxide, 9-aminoacridne; Sigma-Aldrich Company) were used in the test. At the result, there showed no increase in the colony number comparing with positive control, as well as no anti-bacterial activity. On the other hand, there showed significantly increased colony numbers comparing with positive control. Therefore, it has been confirmed that the group treated with KM-3 did not induce reverse mutation in the tested strains.

Experimental Example 28. Micronucleus Test

To evaluate the genetic toxicity, bone marrow micronucleus test using by male ICR mouse was performed according to the method disclosed in the literature (Heddle, J. A., E. Staurt and M. F. Salamone (1984): The bone marrow micronucleus test, In: Handbook of mutagenecity test procedure, $2^{nd}$ Ed., B. J. Kilbey, M. Legator, W. Nichols and C. Ramel, Elsevier Science Publishers BV, pp 441-457). 7-week's aged male ICR mouse was orally administrated with various dose of the test samples, i.e., 0, 500, 1000 and 2000 mg/kg/day for 2 days. 24 hours after the final administration, the bone marrow cell was collected to determine their micronucleus induction and cell toxicity. 2000 polychromatic erythrocyte (PCE)/cell were counted to count the number of micronucleated polychromatic erythrocyte (MN-PCE) with micronucleus.

At the result, there showed no statically significant increase in all the groups treated with the extract comparing with the negative control group treated with 0.5% methyl cellulose in distilled water (0.5% MC). There also showed no statically significant difference between the test group and negative control group in respect to the ratio of polychromatic erythrocyte among total erythrocyte. The ratio of PCE/(PCE+NCE), an indicative of cell cytotoxicity, in all the test groups showed more than 0.35 (mean value) and there showed no significant decrease in all the test groups comparing with negative control group. Accordingly, it has been confirmed that the KM-3 extract did not induce micronucleus in the bone marrow cell of mouse.

Experimental Example 29. Chinese Hamster Lung (CHL) Cell Used Clastogenecity Test To determine the genetic toxicity of the extract on the chromosomal aberration in the mammalian cell, the clastogenecity test using by Chinese hamster lung cell in the presence or absence of metabolic activation system (S-9 mix +S and −S) was performed by the method disclosed in the literature (Richardson, C., Williams, D. A., Alen, J. A., Amphlett, G., Chanter, D. O. and Phillips, B (1989): Analysis of Data from in vitro cytogenetic Assay. In: Statistical Evaluation of Mutagenecity Test Data (Kirkland, D. J. Ed.,), Cambridge University Press, Cambridge, U. K. pp 141-154). The treated concentration of test samples and positive control drugs (Cyclophosphamid H2O (CPA) and Ethylmtanesulfonate (EMS)) was determined through preliminarily test and the determined concentration as shown in Table 12 was set. The samples were treated in the presence (+S, 6 hrs) and absence (−S, 6 and 24 hrs) of metabolic activation system and the resulting chromosomal aberration was counted

TABLE 12

|  | +S | −S |
|---|---|---|
| 6 hrs | 0 μg/ml | 0 μg/ml |
|  | 500 μg/ml | 325 μg/ml |
|  | 1000 μg/ml | 650 μg/ml |
|  | 2000 μg/ml | 1300 μg/ml |
| 24 hrs |  | 0 μg/ml |
|  |  | 250 μg/ml |
|  |  | 500 μg/ml |
|  |  | 900 μg/ml |
|  |  | 1000 μg/ml |
| Positive Control | CPA 12 μg/ml | EMS 800 μg/ml (6 hrs) |
|  |  | EMS 600 μg/ml (24 hrs) |

At the result, the group treated with KM-3 for 6 hrs and 24 hrs did not show statically significant increase in occurring frequency of chromosomal aberration in the presence and absence of metabolic activation system. Accordingly, it has been conformed that the group treated with KM-3 did not induce chromosomal aberration in CHL cell.

Experimental Example 30. HERG Channel Membrane Fraction Binding Assay

To determine the effect of the extract on the potential risk from arrhythmia, hERG channel membrane fraction binding assay based on the founding that the increase of action potential duration among many factors to induce long QT prolongation (induce arrhythmia to cause sudden death is caused by the inhibition of Ikr of K+ channel, was performed by the method disclosed in the literature (Kevin Petrecca, Roxana Atansiu, Armin Akhavan and Alvin Shrier., N-linked glycosylation sites determine HERG channel surface membrane expression., *J. Physiol.*, 1999, 515: 41-48).

In order to determine the current in Ikr channel, hERG DNA which can encode Ikr, was inserted into the vector to form a plasmid, transfect into CHO cell line to express Ikr ion channel. The intensity of current was determined by patch clamp technique, an electro-physiological method, and the inhibition rate, $IC_{50}$, was determined to predict the potential risk of long QT prolongation in accordance with the dosing amount of drug. The dose of KM-3 was determined through following test condition as shown in Table 13.

TABLE 13

| Membrane (origin) | Human ERG K+ channel expressed in HEK-293 cell |
|---|---|
| RI | [3H] Astemizole (4 nM) |
| Buffer solution | 50 mM HEPES (pH 7.4) 60 mM KC10.1% BSA |
| Culture | 60 mins, RT |
| filtration | Filtermat-A/0.3% PEI |

TABLE 14

| | hERG K+ channel | |
|---|---|---|
| Compound | %-Inhibition*(100 g/ml) | IC50 (g/ml) |
| KM-3 | 27.6% | >100 |

As shown in Table 14, the inhibition concentration of KM-3 showed >100 g/ml, which indicates little acute toxicity of cardiovascular. Especially, it has been confirmed that the extract is considered as safe due to very low risk for the potential of sudden death caused by arrhythmia.

Hereinafter, the formulating methods and kinds of excipients will be described, but the present invention is not limited to them. The representative preparation examples were described as follows.
Preparation of Injection
KM-1~4 100 mg
Sodium methabifulfite 3.0 mg
Methyl paraben 0.8 mg
Propyl paraben 0.1 mg
Distilled water for injection optimum amount Injection preparation was prepared by dissolving active component, controlling pH to about 7.5 and then filling all the components in 2 ml ample and sterilizing by conventional injection preparation method.
Preparation of Powder
KM-1~4 500 mg
Corn Starch 100 mg
Lactose 100 mg
Talc 10 mg Powder preparation was prepared by mixing above components and filling sealed package.
Preparation of Tablet
KM-1~4 200 mg
Corn Starch 100 mg
Lactose 100 mg
Magnesium stearate optimum amount Tablet preparation was prepared by mixing above components and entabletting.
Preparation of Capsule
KM-1~4 100 mg
Lactose 50 mg
Corn starch 50 mg
Talc 2 mg
Magnesium stearate optimum amount Tablet preparation was prepared by mixing above components and filling gelatin capsule by conventional gelatin preparation method.

Preparation of Liquid
KM-1~41000 mg
Sugar 20 g
Polysaccharide 20 g
Lemon flavor 20 g Liquid preparation was prepared by dissolving active component, and then filling all the components in 1000 ml ample and sterilizing by conventional liquid preparation method.
Preparation of Health Care Food
KM-1~41000 mg
Vitamin mixture optimum amount
Vitamin A acetate 70 mg
Vitamin E 1.0 mg
Vitamin $B_1$ 0.13 mg
Vitamin $B_2$ 0.15 mg
Vitamin B6 0.5 mg
Vitamin B12 0.2 mg
Vitamin C 10 mg
Biotin 10 mg
Amide nicotinic acid 1.7 mg
Folic acid 50 mg
Calcium pantothenic acid 0.5 mg
Mineral mixture optimum amount
Ferrous sulfate 1.75 mg
Zinc oxide 0.82 mg
Magnesium carbonate 25.3 mg
Monopotassium phosphate 15 mg
Dicalcium phosphate 55 mg
Potassium citrate 90 mg
Calcium carbonate 100 mg
Magnesium chloride 24.8 mg The above mentioned vitamin and mineral mixture may be varied in many ways. Such variations are not to be regarded as a departure from the spirit and scope of the present invention.
Preparation of Health Beverage
KM-1~41000 mg
Citric acid 1000 mg
Oligosaccharide 100 g
Apricot concentration 2 g
Taurine 1 g
Distilled water 900 ml Health beverage preparation was prepared by dissolving active component, mixing, stirred at 85° C. for 1 hour, filtered and then filling all the components in 1000 ml ample and sterilizing by conventional health beverage preparation method.

As described herein, the compositions including the extract of mixed herbs with *Lonicera japonica* THUNB and *Anemarrhena asphodeloides* BUNGE shows potent anti-inflammatory effect through various experiments, therefore, it may be used as the effective and safe therapeutics or health food for treating and preventing arthritic disease.

In this patent, several disclosures have been incorporated by reference. The text of such disclosures is, however, only incorporated by reference to the extent that no conflict exists between such text and the other statements and drawings set forth herein. In the event of such conflict, then any such conflicting text is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating or preventing degenerative arthritis, rheumatic arthritis, or Lupus arthritis comprising administering a therapeutically effective amount of a composition of mixed herbs, the composition comprising a butanol soluble fraction of a 50% ethanol extract of *Lonicera japonica* THUNB and *Anemarrhena asphodeloides* BUNGE, wherein the ratio of *Lonicera japonica* THUNB to *Anemarrhena asphodeloides* BUNGE is 2:1 by weight.

2. The method of claim 1, wherein the composition comprises chlorogenic acid and/or mangiferin.

3. The method of claim 2, wherein the composition comprises 0.5 to 6% (w/w) chlorogenic acid and 0.5 to 4% (w/w) mangiferin as a standard component.

* * * * *

```
                         SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Col II for sense primer

<400> SEQUENCE: 1
aacactgcca acgtccagat                                                  20

<210> SEQ ID NO 2
<211> LENGTH: 20
<212> TYPE: DNA
<213> ORGANISM: Artificial Sequence
<220> FEATURE:
<223> OTHER INFORMATION: Col II for anti-sense primer

<400> SEQUENCE: 2
ctgcagcacg gtataggtga                                                  20

<210> SEQ ID NO 3
<211> LENGTH: 20
<212> TYPE: DNA
<213> ORGANISM: Artificial Sequence
<220> FEATURE:
<223> OTHER INFORMATION: PG for sense primer

<400> SEQUENCE: 3
gaggtcgtgg tgaaaggtgt                                                  20

<210> SEQ ID NO 4
<211> LENGTH: 20
<212> TYPE: DNA
<213> ORGANISM: Artificial Sequence
<220> FEATURE:
<223> OTHER INFORMATION: PG for anti-sense primer

<400> SEQUENCE: 4
gtgtggatgg ggtacctgac                                                  20

<210> SEQ ID NO 5
<211> LENGTH: 19
<212> TYPE: DNA
<213> ORGANISM: Artificial Sequence
<220> FEATURE:
<223> OTHER INFORMATION: MMP-1 for sense primer

<400> SEQUENCE: 5
aaagggaata agtactggg                                                   19

<210> SEQ ID NO 6
<211> LENGTH: 22
<212> TYPE: DNA
<213> ORGANISM: Artificial Sequence
<220> FEATURE:
<223> OTHER INFORMATION: MMP-1 for anti-sense primer

<400> SEQUENCE: 6
```
gtttttccag tgttttcctc ag                                                   22

<210> SEQ ID NO 7
<211> LENGTH: 21
<212> TYPE: DNA
<213> ORGANISM: Artificial Sequence
<220> FEATURE:
<223> OTHER INFORMATION: MMP-3 for sense primer

<400> SEQUENCE: 7
tgcgtggcag tttgctcagc c                                                    21

<210> SEQ ID NO 8
<211> LENGTH: 21
<212> TYPE: DNA
<213> ORGANISM: Artificial Sequence
<220> FEATURE:
<223> OTHER INFORMATION: MMP-3 for anti-sense primer

<400> SEQUENCE: 8
gaatgtgagt ggagtcacct c                                                    21

<210> SEQ ID NO 9
<211> LENGTH: 19
<212> TYPE: DNA
<213> ORGANISM: Artificial Sequence
<220> FEATURE:
<223> OTHER INFORMATION: MMP-13 for sense primer

<400> SEQUENCE: 9
gataaagact atccgagac                                                       19

<210> SEQ ID NO 10
<211> LENGTH: 18
<212> TYPE: DNA
<213> ORGANISM: Artificial Sequence
<220> FEATURE:
<223> OTHER INFORMATION: MMP-13 for anti-sense primer

<400> SEQUENCE: 10
cgaacaatac ggttactc                                                        18

<210> SEQ ID NO 11
<211> LENGTH: 16
<212> TYPE: DNA
<213> ORGANISM: Artificial Sequence
<220> FEATURE:
<223> OTHER INFORMATION: OCN for sense primer

<400> SEQUENCE: 11
catgagagcc ctcaca                                                          16

<210> SEQ ID NO 12
<211> LENGTH: 17
<212> TYPE: DNA
<213> ORGANISM: Artificial Sequence
<220> FEATURE:
<223> OTHER INFORMATION: OCN for anti-sense primer

<400> SEQUENCE: 12
agagcgacac cctagac                                                         17

<210> SEQ ID NO 13
<211> LENGTH: 20
<212> TYPE: DNA
<213> ORGANISM: Artificial Sequence

```
<220> FEATURE:
<223> OTHER INFORMATION: Col I for sense primer

<400> SEQUENCE: 13
tgacctcaag atgtgccact                                                   20

<210> SEQ ID NO 14
<211> LENGTH: 20
<212> TYPE: DNA
<213> ORGANISM: Artificial Sequence
<220> FEATURE:
<223> OTHER INFORMATION: Col I for anti-sense primer

<400> SEQUENCE: 14
gggagtttcc atgaagccac                                                   20

<210> SEQ ID NO 15
<211> LENGTH: 24
<212> TYPE: DNA
<213> ORGANISM: Artificial Sequence
<220> FEATURE:
<223> OTHER INFORMATION: GAPDH for sense primer

<400> SEQUENCE: 15
gctctccaga acatcatccc tgcc                                              24

<210> SEQ ID NO 16
<211> LENGTH: 24
<212> TYPE: DNA
<213> ORGANISM: Artificial Sequence
<220> FEATURE:
<223> OTHER INFORMATION: GAPDH for anti-sense primer

<400> SEQUENCE: 16
cgttgtcata ccaggaaatg agct                                              24
```